(12) United States Patent
Klar et al.

(10) Patent No.: US 8,937,058 B2
(45) Date of Patent: Jan. 20, 2015

(54) 17-HYDROXY-19-NOR-21-CARBOXYLIC ACID-STEROID γ-LACTONE DERIVATIVE, USE THEREOF, AND MEDICAMENT CONTAINING THE DERIVATIVE

(76) Inventors: Ulrich Klar, Berlin (DE); Joachim Kuhnke, Potsdam (DE); Rolf Bohlmann, Berlin (DE); Jan Hübner, Berlin (DE); Sven Ring, Jena (DE); Thomas Frenzel, Hofheim (DE); Frederik Menges, Schriesheim (DE); Steffen Borden, Berlin (DE); Hans-Peter Muhn, Berlin (DE); Katja Prelle, Berlin (DE)

( * ) Notice: Subject to any disclaimer, the term of this patent is extended or adjusted under 35 U.S.C. 154(b) by 430 days.

(21) Appl. No.: 12/810,991

(22) PCT Filed: Dec. 23, 2008

(86) PCT No.: PCT/EP2008/011159
§ 371 (c)(1), (2), (4) Date: Oct. 4, 2010

(87) PCT Pub. No.: WO2009/083266
PCT Pub. Date: Jul. 9, 2009

(65) Prior Publication Data
US 2011/0021472 A1  Jan. 27, 2011

(30) Foreign Application Priority Data
Dec. 29, 2007 (DE) .......................... 10 2007 063 503

(51) Int. Cl.
| | | |
|---|---|---|
| A61K 31/585 | (2006.01) | |
| C07J 21/00 | (2006.01) | |
| C07J 53/00 | (2006.01) | |
| C07J 19/00 | (2006.01) | |

(52) U.S. Cl.
CPC . *C07J 53/00* (2013.01); *C07J 19/00* (2013.01)
USPC ............................................. 514/173; 540/41

(58) Field of Classification Search
CPC .............................. C07J 21/003; A61K 31/585
USPC ............................................ 514/173; 540/41
See application file for complete search history.

(56) References Cited

U.S. PATENT DOCUMENTS

| | | | | |
|---|---|---|---|---|
| 2,918,463 | A * | 12/1959 | Cella ................................ | 540/41 |
| 3,194,803 | A * | 7/1965 | Colton ............................ | 540/41 |
| 3,254,074 | A * | 5/1966 | Arth et al. ......................... | 540/7 |
| 3,764,596 | A | 10/1973 | Galantay | |
| 4,502,989 | A * | 3/1985 | Kamata et al. .................... | 540/15 |
| 4,891,365 | A * | 1/1990 | Wiechert et al. ............... | 514/173 |
| 5,827,842 | A | 10/1998 | Schollkopf et al. | |

FOREIGN PATENT DOCUMENTS

| | | |
|---|---|---|
| DE | 3022337 A1 | 1/1982 |
| DE | 3426771 | 1/1986 |
| DE | 4447401 A1 | 7/1996 |
| WO | 94/06819 | 3/1994 |
| WO | 2006072467 A1 | 7/2006 |
| WO | PCTEP2008011159 R | 4/2009 |

OTHER PUBLICATIONS

Klaus Nickish, Sybille Beier, Dieter Bittler, Walter Elger, Henry Laurent, Wolfgang Losert, Yukishige Nishino, Ekkehard Schillenger, and Rudolf Wiechert, "Aldosterone Antagonists. 4. Synthesis and Activities of Steroidal 6,6-Ethylene-15,16-methylene 17 Spirolactones," J. Med. Chem., vol. 34, pp. 2464-2468 (1991).

* cited by examiner

*Primary Examiner* — Barbara P Badio
(74) *Attorney, Agent, or Firm* — Thomas C. Blankinship; Karen B. King

(57) ABSTRACT

The invention relates to 17-hydroxy-19-nor-21-carboxylic acid-steroid γ-lactone derivatives with the chemical formula I, where $R^4$, $R^{6a}$, $R^{6b}$, $R^7$, $R^{15}$, $R^{16a}$, $R^{16b}$, $R^{18}$ and Z have the meanings stated in claim 1, and their solvates, hydrates, stereoisomers and salts. The invention further relates to the use of these derivatives for the production of a medicinal product for oral contraception and for the treatment of pre-, peri- and postmenopausal complaints and medicinal products that contain said derivatives. The derivatives according to the invention have a progestational and in preferred cases additionally an antimineralocorticoid and neutral to slightly androgenic action.

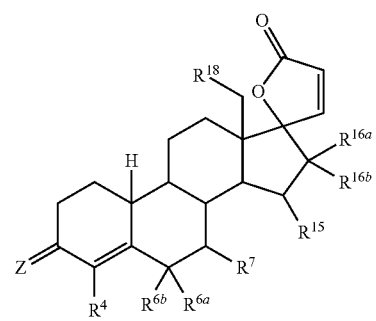

I

11 Claims, No Drawings

17-HYDROXY-19-NOR-21-CARBOXYLIC ACID-STEROID γ-LACTONE DERIVATIVE, USE THEREOF, AND MEDICAMENT CONTAINING THE DERIVATIVE

The invention relates to certain 17-hydroxy-19-nor-21-carboxylic acid-steroid γ-lactone derivatives, use thereof and medicinal products containing the derivatives with progestational action, for example for the treatment of pre-, peri- and postmenopausal and of premenstrual complaints.

Compounds with progestational, antimineralocorticoid, antiandrogenic or antiestrogenic action based on a steroid structure are known from the literature, derived for example from 19-nor-androst-4-en-3-one or a derivative thereof (the numbering of the steroid structure is given for example in Fresenius/Görlitzer 3rd Ed. 1991 "Organic-Chemical Nomenclature" p. 60 ff.).

Thus, WO 2006072467 A1 discloses the compound 6β,7β;15γ,16β-dimethylene-3-oxo-17-pregn-4-ene-21,17β-carbolactone (drospirenone), which has progestational action and has been used for example in an oral contraceptive and in a preparation for the treatment of postmenopausal complaints. Owing to its comparatively low affinity for the progestogen receptor and its comparatively high ovulation-inhibiting dose, however, drospirenone is contained in the contraceptive at the relatively high daily dose of 3 mg. Drospirenone is, moreover, also characterized in that in addition to the progestational action it also has aldosterone-antagonistic (antimineralocorticoid) and antiandrogenic action. These two properties make drospirenone very similar in its pharmacological profile to the natural progestogen, progesterone, which however, unlike drospirenone, is not sufficiently bioavailable orally. In order to lower the dose to be administered, WO 2006072467 A1 further proposes an 18-methyl-19-nor-17-pregn-4-ene-21,17-carbolactone and pharmaceutical preparations containing this, which have a higher progestational potency than drospirenone.

In addition, U.S. Pat. No. 3,705,179, for example, discloses steroids that display antiandrogenic activity and are suitable for the treatment of diseases that are linked to androgens.

Furthermore, U.S. Pat. No. 2,918,463 discloses 17-carboxyalkylated 17-hydroxy-19-nor-androsten-3-ones, including 17α-(2-carboxyvinyl)-17β-hydroxy-19-nor-androst-4-en-3-one lactone. The compounds described are said to block the action of deoxycorticosterone acetate on the level of sodium and potassium in the urine and simultaneously, at higher concentration, have a salt-binding action. Moreover, these compounds are also said to be effective against hypertension.

The aim of the present invention is to make compounds available that bind strongly to the progestogen receptor. Moreover, the compounds should preferably also have antimineralocorticoid action and, with respect to the androgen receptor, a neutral to slightly androgenic action. Another essential aim of the present invention consists of achieving a balanced action profile with respect to the progestational action to the antimineralocorticoid action, so that the ratio of the progestational action to the antimineralocorticoid action is less than with drospirenone.

This aim is achieved with the 17-hydroxy-19-nor-21-carboxylic acid-steroid γ-lactone derivatives according to the invention according to claim 1, the use of the derivatives according to the invention according to claim 17 and a medicinal product containing at least one derivative according to the invention according to claim 19. Advantageous embodiments of the invention are given in the subclaims.

Accordingly, the invention relates to a 17-hydroxy-19-nor-21-carboxylic acid-steroid γ-lactone derivative with the following chemical formula I:

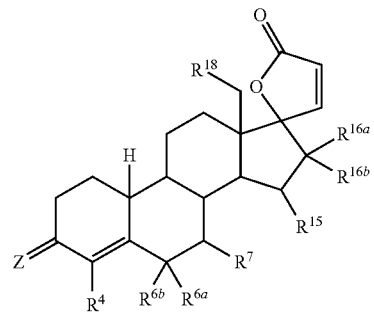

in which
Z is selected from the group comprising oxygen, two hydrogen atoms, NOR' and NNHSO$_2$R', in which R' is hydrogen, $C_1$-$C_{10}$-alkyl, aryl or $C_7$-$C_{20}$-aralkyl,
$R^4$ is selected from the group comprising hydrogen and halogen,
in addition either:
$R^{6a}$, $R^{6b}$ in each case independently of one another, are selected from the group comprising hydrogen, $C_1$-$C_{10}$-alkyl, $C_2$-$C_{10}$-alkenyl and $C_2$-$C_{10}$-alkynyl, or together form methylene or 1,2-ethanediyl and
$R^7$ is selected from the group comprising hydrogen, $C_1$-$C_{10}$-alkyl, $C_3$-$C_6$-cycloalkyl, $C_2$-$C_{10}$-alkenyl and $C_2$-$C_{10}$-alkynyl,
or:
$R^{6a}$, $R^7$ together form an oxygen atom or methylene or are omitted with formation of a double bond between $C^6$ and $C^7$ and
$R^{6b}$ is selected from the group comprising hydrogen, $C_1$-$C_{10}$-alkyl, $C_2$-$C_{10}$-alkenyl and $C_2$-$C_{10}$-alkynyl,
in addition either:
$R^{15}$ is hydrogen and
$R^{16a}$, $R^{16b}$ in each case independently of one another, are selected from the group comprising hydrogen and $C_1$-$C_{10}$-alkyl, or together form methylene or 1,2-ethanediyl
or:
$R^{15}$, $R^{16a}$ together form an oxygen atom or are omitted with formation of a double bond between $C^{15}$ and $C^{16}$ and
$R^{16b}$ is hydrogen or $C_1$-$C_{10}$-alkyl,
$R^{18}$ is hydrogen or $C_1$-$C_3$-alkyl,
and their solvates, hydrates, stereoisomers and salts,
with the proviso that 17α-(2-carboxyvinyl)-17β-hydroxy-19-nor-androst-4-en-3-one γ-lactone (17β-hydroxy-19-nor-17α-pregna-4,20(Z)-dien-3-one-21-carboxylic acid γ-lactone) is excluded.

The numbering of the carbon backbone of the derivative according to the invention with the general chemical formula I follows the numbering of a steroid structure in the usual way, described for example in Fresenius, loc. cit. The numbering of the residues stated in the claims similarly corresponds to their binding position on the carbon backbone of the derivative, if this relates to $R^4$, $R^6$, $R^7$, $R^{15}$, $R^{16}$ and $R^{18}$. For example, the residue $R^4$ binds to the $C^4$-position of the derivative according to the invention.

With respect to the groups defined under Z, the groups NOR' and NNHSO$_2$R' each bind with a double bond via N to the carbon backbone of the derivative according to =NOR' or =NNH—SO$_2$R'. OR' in NOR' and NHSO$_2$R' in NNHSO$_2$R' can be in syn- or anti-position.

Alkyl in R', R$^{6a}$, R$^{6b}$, R$^7$, R$^{16a}$ and R$^{16b}$ and in R$^{19}$, R$^{20}$, R$^{21a}$, R$^{21b}$ and R$^{22}$ in the further general chemical formulae given later represents linear or branched alkyl groups with 1-10 carbon atoms, for example methyl, ethyl, propyl, isopropyl, butyl, isobutyl, tert.-butyl, pentyl, isopentyl, neopentyl, heptyl, hexyl, decyl. Alkyl in R$^{18}$ means in particular methyl, ethyl, propyl or isopropyl. The alkyl groups R', R$^{6a}$, R$^{6b}$, R$^7$, R$^{16a}$, R$^{16b}$ and R$^{18}$ can moreover be perfluorinated or can be substituted with 1-5 halogen atoms, hydroxyl groups, C$_1$-C$_4$-alkoxy groups, C$_6$-C$_{12}$-aryl groups (which in their turn can be substituted with 1-3 halogen atoms). In particular, therefore, alkyl can also stand for hydroxymethylene (HO—CH$_2$), hydroxyethylene (HO—C$_2$H$_4$), hydroxypropylene (HO—C$_3$H$_6$) and hydroxybutylene (HO—C$_4$H$_8$) and their isomers.

Alkenyl in R$^{6a}$, R$^{6b}$ and R$^7$ means linear or branched alkenyl groups with 2-10 carbon atoms, for example vinyl, propenyl, butenyl, pentenyl, isobutenyl, isopentenyl.

Alkynyl in R$^{6a}$, R$^{6b}$ and R$^7$ means linear or branched alkynyl groups with 2-10 carbon atoms, for example ethynyl, propynyl, butynyl, pentynyl, isobutynyl, isopentynyl.

The alkenyl and alkynyl groups R$^{6a}$, R$^{6a}$ and R$^7$ can be substituted with 1-5 halogen atoms, hydroxyl groups, C$_1$-C$_3$-alkoxy groups, C$_6$-C$_{12}$-aryl groups (which in their turn can be substituted with 1-3 halogen atoms).

Cycloalkyl in R$^7$ means cycloalkyl groups with 3-6 carbon atoms, for example cyclopropyl, cyclobutyl, cyclopentyl and cyclohexyl. The cycloalkyl groups R$^7$ can be substituted with halogen, OH, O-alkyl, CO$_2$H, CO$_2$-alkyl, NH$_2$, NO$_2$, N$_3$, CN, C$_1$-C$_{10}$-alkyl, C$_1$-C$_{10}$-acyl, C$_1$-C$_{10}$-acyloxy groups.

Aryl in R' means substituted and unsubstituted carbocyclic or heterocyclic residues with one or more heteroatoms, for example phenyl, naphthyl, furyl, thienyl, pyridyl, pyrazolyl, pyrimidinyl, oxazolyl, pyridazinyl, pyrazinyl, quinolyl, thiazolyl, which can be substituted singly or multiply with halogen, OH, O-alkyl, CO$_2$H, CO$_2$-alkyl, NH$_2$, NO$_2$, N$_3$, CN, C$_1$-C$_{10}$-alkyl, C$_1$-C$_{10}$-acyl, C$_1$-C$_{10}$-acyloxy groups. In so far as aryl is otherwise mentioned as substituent on alkyl, alkenyl or alkynyl, it relates in particular to aryl groups with 6-12 ring carbon atoms.

Aralkyl in R' and R$^7$ means aralkyl groups that can contain up to 14 carbon atoms, preferably 6 to 10 carbon atoms, in the ring, and 1 to 8, preferably 1 to 4, carbon atoms in the alkyl chain. As aralkyl residues, consideration may be given for example to benzyl, phenylethyl, naphthylmethyl, naphthylethyl, furylmethyl, thienylethyl, pyridylpropyl. The rings can be substituted singly or multiply with halogen, OH, O-alkyl, CO$_2$H, CO$_2$-alkyl, NO$_2$, N$_3$, CN, C$_1$-C$_{20}$-alkyl, C$_1$-C$_{20}$-acyl, C$_1$-C$_{20}$-acyloxy groups.

If alkoxy (O-alkyl) is mentioned as substituent on alkyl, it refers to alkoxy groups with 1-4 carbon atoms, and if alkoxy is mentioned as substituent on alkenyl and alkynyl, it refers to alkoxy groups with 1-3 carbon atoms. Alkoxy can in particular be methoxy, ethoxy and propoxy.

If acyl (CO-alkyl) is mentioned as substituent on cycloalkyl and aryl, it refers to acyl groups with 1-10 carbon atoms, and if acyl is mentioned as substituent on aralkyl, it refers to acyl groups with 1-20 carbon atoms. Acyl can in particular be formyl, acetyl, propionyl and butyryl.

If acyloxy (O—CO-alkyl) is mentioned as substituent on cycloalkyl and aryl, it refers to acyloxy groups with 1-10 carbon atoms, and if acyloxy is mentioned as substituent on aralkyl, it refers to acyloxy groups with 1-20 carbon atoms. Acyloxy can in particular be formyloxy, acetyloxy, propionyloxy and butyryloxy.

Halogen means fluorine, chlorine or bromine.

According to a preferred embodiment of the invention, Z is selected from the group comprising oxygen, NOR' and NNHSO$_2$R'.

According to another preferred embodiment of the invention Z stands for oxygen.

According to another preferred embodiment of the invention, R$^4$ is hydrogen or chlorine.

According to another preferred embodiment of the invention R$^{6a}$, R$^{6b}$ together form 1,2-ethanediyl or are each hydrogen.

According to another preferred embodiment of the invention, R$^7$ is selected from the group comprising hydrogen, methyl, ethyl and vinyl.

According to another preferred embodiment of the invention R$^{6a}$, R$^7$ together form methylene.

According to another preferred embodiment of the invention R$^{6a}$ and R$^7$ drop out, with formation of a double bond between C$^6$ and C$^7$.

According to another preferred embodiment of the invention, R$^{15}$ is hydrogen.

According to another preferred embodiment of the invention, R$^{15}$, R$^{16a}$ drop out, with formation of a double bond between C$^{15}$ and C$^{16}$ or R$^{15}$, R$^{16a}$ together form an oxygen atom.

According to another preferred embodiment of the invention R$^{16a}$ is hydrogen and R$^{16b}$ is methyl.

According to another preferred embodiment of the invention R$^{16a}$ and R$^{16b}$ are hydrogen.

According to another preferred embodiment of the invention R$^{16a}$ and R$^{16b}$ together form methylene or 1,2-ethanediyl.

According to another preferred embodiment of the invention, R$^{18}$ is hydrogen or methyl.

Compounds with the chemical formula I are preferred, in which

Z is oxygen, a group NOR', where R' is hydrogen, C$_1$-C$_6$-alkyl, aryl or C$_7$-C$_{12}$-aralkyl, R$^4$ is hydrogen or halogen, and either:

R$^{6a}$, R$^{6b}$ independently of one another are hydrogen, C$_1$-C$_6$-alkyl, C$_2$-C$_6$-alkenyl or C$_2$-C$_6$-alkynyl or together form methylene or 1,2-ethanediyl and R$^7$ is hydrogen, C$_1$-C$_6$-alkyl, C$_3$-C$_6$-cycloalkyl, C$_2$-C$_6$-alkenyl or C$_2$-C$_6$-alkynyl, or:

R$^{6a}$, R$^7$ are omitted with formation of a double bond between C$^6$ and C$^7$ or together form methylene and R$^{6b}$ is selected from the group comprising hydrogen, C$_1$-C$_6$-alkyl, C$_2$-C$_6$-alkenyl and C$_2$-C$_6$-alkynyl, in addition either:

R$^{15}$ is hydrogen and

R$^{16a}$, R$^{16b}$ independently of one another are hydrogen or C$_1$-C$_6$-alkyl or together form methylene or 1,2-ethanediyl, or:

R$^{15}$, R$^{16a}$ are omitted with formation of a double bond between C$^{15}$ and C$^{16}$ and R$^{16b}$ is hydrogen or C$_1$-C$_6$-alkyl, R$^{18}$ is hydrogen, methyl or ethyl.

Compounds of formula I are especially preferred in which

Z is oxygen or a group NOR', and R' is hydrogen or C$_1$-C$_3$-alkyl,

R$^4$ is hydrogen, chlorine or bromine, and either:

R$^{6a}$, R$^{6b}$ independently of one another are hydrogen, C$_1$-C$_3$-alkyl or C$_2$-C$_4$-alkenyl or together form methylene or 1,2-ethanediyl and $R^7$ is hydrogen, $C_1$-$C_4$-alkyl, $C_3$-$C_4$-cycloalkyl or $C_2$-$C_4$-alkenyl, or:

$R^{6a}$, $R^7$ are omitted with formation of a double bond between $C^6$ and $C^7$ or together form methylene and $R^{6b}$ is hydrogen, $C_1$-$C_3$-alkyl or $C_2$-$C_4$-alkenyl, in addition either:

$R^{15}$ is hydrogen and $R^{16a}$, $R^{16b}$ are hydrogen or together form methylene or 1,2-ethanediyl, or:

$R^{15}$, $R^{16a}$ are omitted with formation of a double bond between $C^{15}$ and $C^{16}$ and $R^{16b}$ is hydrogen, $R^{18}$ is hydrogen or methyl.

All possible stereoisomers and isomeric mixtures, including racemates, of the compound with the general chemical formula I are hereby expressly included, and moreover the position of the unsaturated γ-lactone ring in the derivative according to the invention can also occur in two isomeric forms. Each of the stated substituents on the steroid basic structure can be both in an α position and in a β position. Furthermore, the substituents on the steroid basic structure that contain a double bond and in which the double bond to each carbon atom carries at least one substituent, which is not hydrogen, can be both E- and Z-configured. Groups bound to two adjacent carbon atoms of the structure, for example an oxygen atom, methylene or 1,2-ethanediyl, are bound either in α,α-position or in β,β-position.

All crystal modifications of the compound with the general chemical formula I are also expressly included.

Derivatives according to the invention in the form of solvates, in particular of hydrates, are also expressly included, and the compounds according to the invention can accordingly contain polar solvents, in particular water, as structural element of the crystal lattice of the compounds according to the invention. The polar solvent, in particular water, can be present in stoichiometric proportions or even in nonstoichiometric proportions.

Stoichiometric solvates and hydrates are also called hemi-, (semi-), mono-, sesqui-, di-, tri-, tetra-, penta-, etc. solvates or hydrates.

If an acid function is present, the physiologically compatible salts of organic and inorganic bases are suitable as salts, for example the readily soluble alkali-metal and alkaline-earth salts, and the salts of N-methyl-glucamine, D-methyl-glucamine, ethyl-glucamine, lysine, 1,6-hexadiamine, ethanolamine, glucosamine, sarcosine, serinol, Tris-hydroxy-methyl-aminomethane, aminopropanediol, Sovak-base, 1-amino-2,3,4-butanetriol. If a basic function is present, the physiologically compatible salts of organic and inorganic acids are suitable, such as of hydrochloric acid, sulfuric acid, phosphoric acid, citric acid, tartaric acid etc.

It was found that the compounds or derivatives according to the invention have good progestational action. Furthermore, some interesting compounds according to the invention interact with the mineralocorticoid receptor and are able to impart an antagonistic action. Moreover, the compounds according to the invention have a neutral to slightly androgenic action with respect to the androgen receptor. Another property of the majority of the compounds is that the bonds of these compounds to the progesterone receptor and to the mineralocorticoid receptor are balanced relative to one another, namely so that their ratio of the capacity for binding to the progesterone receptor to the capacity for binding to the mineralocorticoid receptor is less than in the case of drospirenone. Therefore the antimineralocorticoid action of these compounds at given progestational action is less than with drospirenone. If the dosage of a given compound according to the invention is based on its progestational action, the antimineralocorticoid action of this compound at this dosage is therefore less than with drospirenone.

The compounds listed below are especially preferred according to the invention:

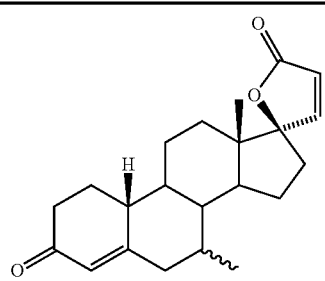

17β-Hydroxy-7α-methyl-19-nor-17α-pregna-4,20(Z)-dien-3-one-21-carboxylic acid γ-lactone (Example 2A)

17β-Hydroxy-7β-methyl-19-nor-17α-pregna-4,20(Z)-dien-3-one-21-carboxylic acid γ-lactone (Example 2B)

17β-Hydroxy-7α-ethyl-19-nor-17α-pregna-4,20(Z)-dien-3-one-21-carboxylic acid γ-lactone (Example 3A)

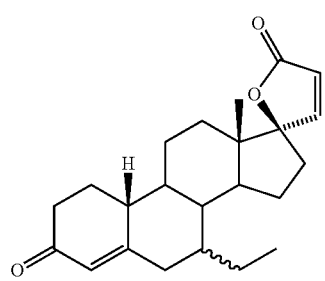 [SMILES: CCC1CC2=CC(=O)CC[C@@H]2C2CC[C@@]3(C)C(CC[C@@]34C=CC(=O)O4)C12]

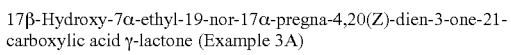

17β-Hydroxy-7β-ethyl-19-nor-17α-pregna-4,20(Z)-dien-3-one-21-carboxylic acid γ-lactone (Example 3B)

-continued

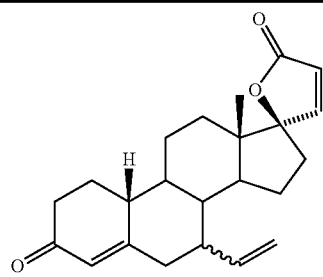

17β-Hydroxy-7α-vinyl-19-nor-17α-pregna-4,20(Z)-dien-3-one-21-carboxylic acid γ-lactone (Example 4A)

17β-Hydroxy-7β-vinyl-19-nor-17α-pregna-4,20(Z)-dien-3-one-21-carboxylic acid γ-lactone (Example 4B)

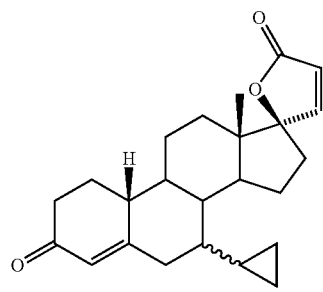 [SMILES: C[C@]12CCC3C(C(C4CC4)CC4=CC(=O)CC[C@@H]43)C1CC[C@@]21C=CC(=O)O1]

17β-Hydroxy-7α-cyclopropyl-19-nor-17α-pregna-4,20(Z)-dien-3-one-21-carboxylic acid γ-lactone (Example 12A)

17β-Hydroxy-7β-vinyl-19-nor-17α-pregna-4,20(Z)-dien-3-one-21-carboxylic acid γ-lactone (Example 12B)

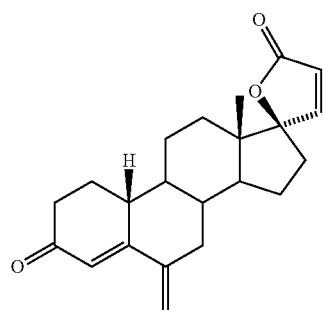 [SMILES: C=C1CC2C(CC[C@@]3(C)C2CC[C@@]32C=CC(=O)O2)[C@H]2CCC(=O)C=C12]

17β-Hydroxy-6-methylene-19-nor-17α-pregna-4,20(Z)-dien-3-one-21-carboxylic acid γ-lactone

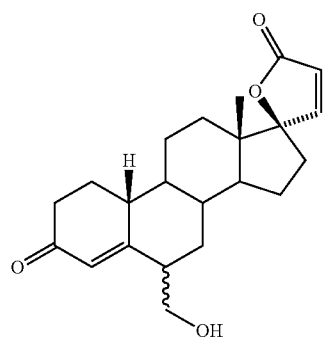 [SMILES: C[C@]12CCC3C(CC(CO)C4=CC(=O)CC[C@@H]43)C1CC[C@@]21C=CC(=O)O1]

17β-Hydroxy-6α-hydroxymethylene-19-nor-17α-pregna-4,20(Z)-dien-3-one-21-carboxylic acid γ-lactone
17β-Hydroxy-6β-hydroxymethylene-19-nor-17α-pregna-4,20(Z)-dien-3-one-21-carboxylic acid γ-lactone (Example 17)

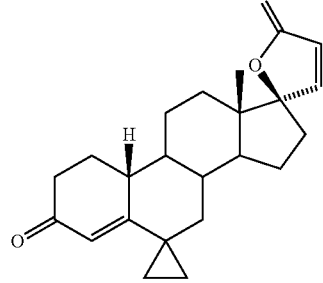

6,6-(1,2-Ethanediyl)-17β-hydroxy-19-nor-17α-pregna-4,20(Z)-dien-3-one-21-carboxylic acid γ-lactone (Example 18)

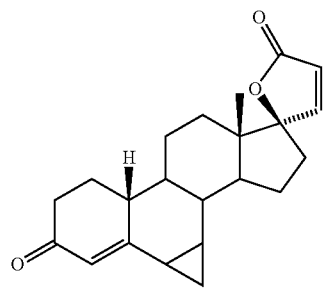 [SMILES: C[C@]12CCC3C(C4CC4C4=CC(=O)CC[C@@H]43)C1CC[C@@]21C=CC(=O)O1]

17β-Hydroxy-6α,7α-methylene-19-nor-17α-pregna-4,20(Z)-dien-3-one-21-carboxylic acid γ-lactone (Example 20B)
17β-Hydroxy-6β,7β-methylene-19-nor-17α-pregna-4,20(Z)-dien-3-one-21-carboxylic acid γ-lactone (Example 20A)

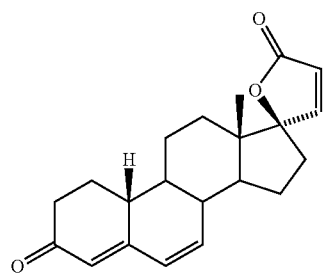 [SMILES: C[C@]12CCC3C(C=CC4=CC(=O)CC[C@@H]43)C1CC[C@@]21C=CC(=O)O1]

17β-Hydroxy-19-nor-17α-pregna-4,20(Z)-trien-3-one-21-carboxylic acid γ-lactone (Example 1)

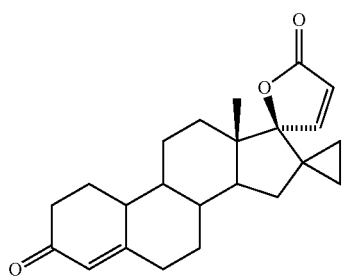 [SMILES: C[C@]12CCC3C4CCC(=O)C=C4CCC3C1CC1(CC1)[C@@]21C=CC(=O)O1]

16,16-(1,2-Ethanediyl)-17β-hydroxy-19-nor-17α-pregna-4,20(Z)-dien-3-one-21-carboxylic acid γ-lactone (Example 5)

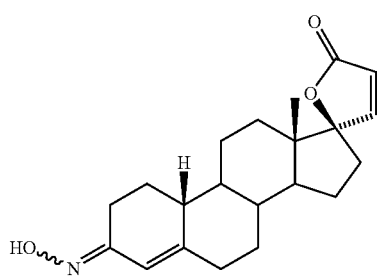 [SMILES: C[C@]12CCC3C(CCC4=CC(=NO)CC[C@@H]43)C1CC[C@@]21C=CC(=O)O1]

(E/Z)-3-(Hydroxyimino)-17β-hydroxy-19-nor-17α-pregna-4,20(Z)-diene-21-carboxylic acid γ-lactone

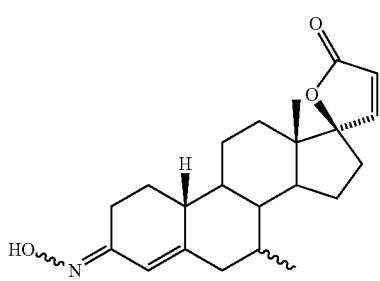 [SMILES: CC1CC2=CC(=NO)CC[C@@H]2C2CC[C@@]3(C)C(CC[C@@]34C=CC(=O)O4)C12]

(E/Z)-3-(Hydroxyimino)-17β-hydroxy-7α-methyl-19-nor-17α-pregna-4,20(Z)-diene-21-carboxylic acid γ-lactone (E/Z)-3-(Hydroxyimino)-17β-hydroxy-7β-methyl-19-nor-17α-pregna-4,20(Z)-diene-21-carboxylic acid γ-lactone

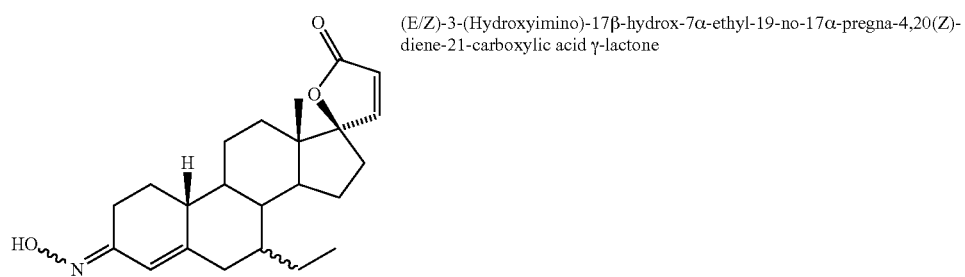

(E/Z)-3-(Hydroxyimino)-17β-hydrox-7α-ethyl-19-no-17α-pregna-4,20(Z)-diene-21-carboxylic acid γ-lactone (E/Z)-3-(Hydroxyimino)-17β-hydroxy-7β-ethyl-19-nor-17α-pregna-4,20(Z)diene-21-carboxylic acid γ-lactone

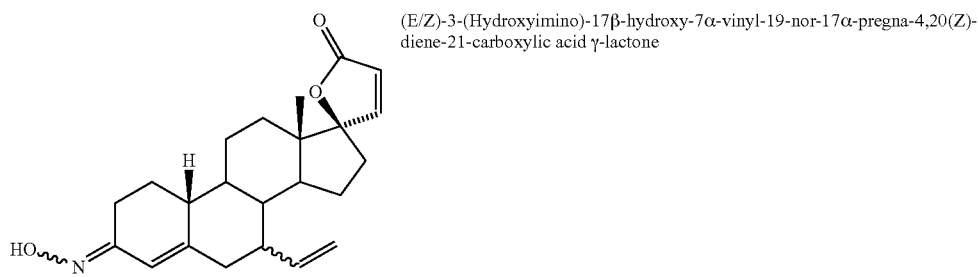

(E/Z)-3-(Hydroxyimino)-17β-hydroxy-7α-vinyl-19-nor-17α-pregna-4,20(Z)-diene-21-carboxylic acid γ-lactone (E/Z)-3-(Hydroxyimino)-17β-hydroxy-7β-vinyl-19-nor-17α-pregna-4,20(Z)-diene-21-carboxylic acid γ-lactone (E/Z)-3-(Hydroxyimino)-17β-hydroxy-7α-cyclopropyl-19-nor-17α-pregna-4,20(Z)-diene-21-carboxylic acid γ-lactone

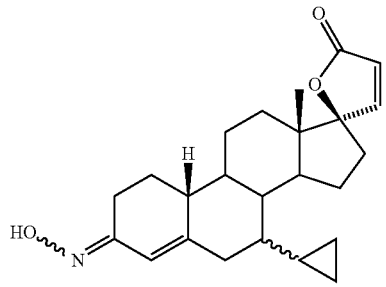 [SMILES: C[C@]12CCC3C(C(C4CC4)CC4=CC(=NO)CC[C@@H]43)C1CC[C@@]21C=CC(=O)O1]

(E/Z)-3-(Hydroxyimino)-17β-hydroxy-7β-cyclopropyl-19-nor-17α-pregna-4,20(Z)-diene-21-carboxylic acid γ-lactone (E/Z)-3-(Hydroxyimino)-17β-hydroxy-6-methylene-19-nor-17α-pregna-4,20(Z)-diene-21-carboxylic acid γ-lactone

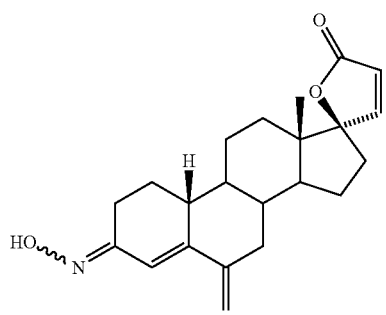

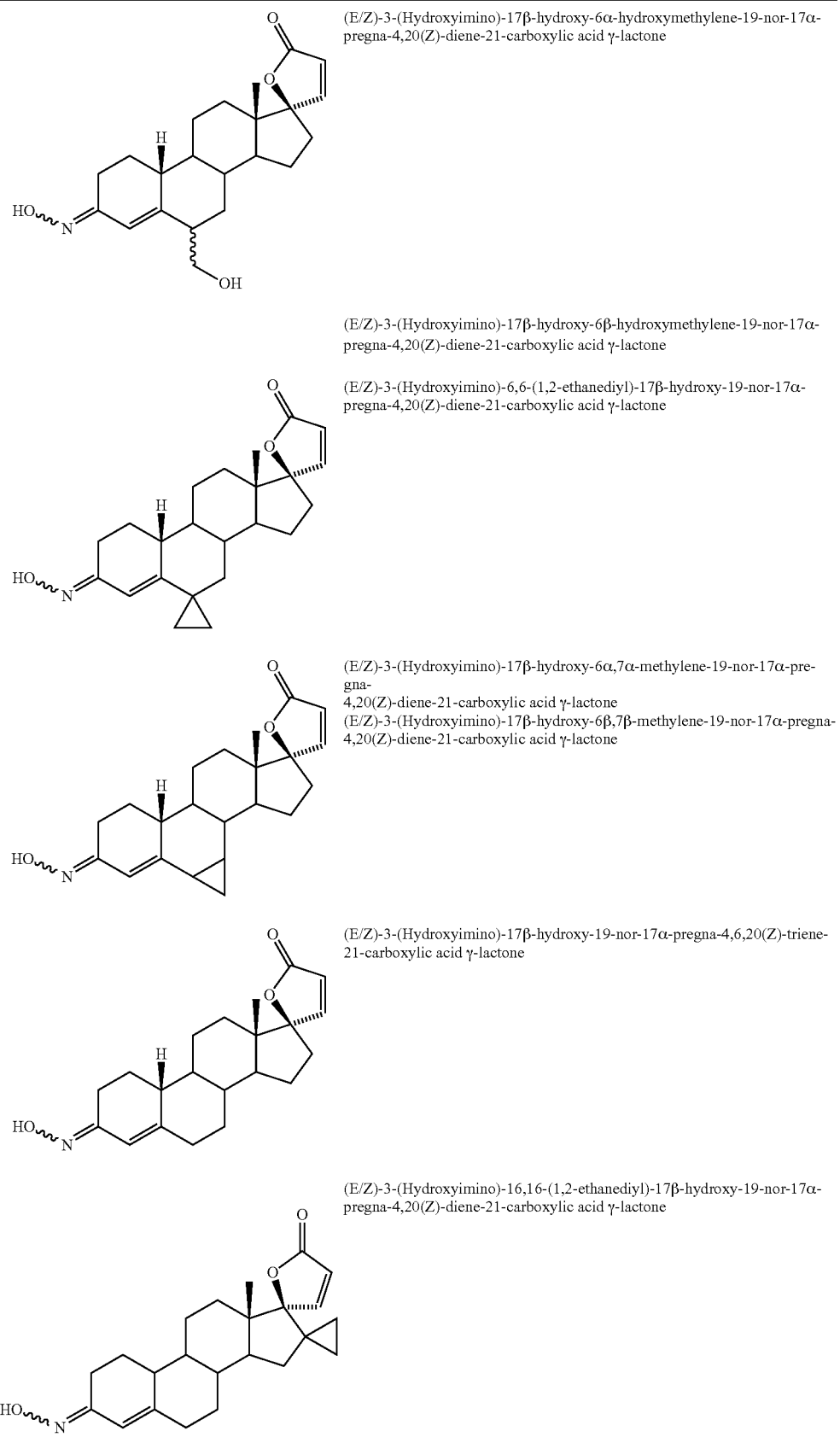

(E/Z)-3-(Hydroxyimino)-17β-hydroxy-6α-hydroxymethylene-19-nor-17α-pregna-4,20(Z)-diene-21-carboxylic acid γ-lactone (E/Z)-3-(Hydroxyimino)-17β-hydroxy-6β-hydroxymethylene-19-nor-17α-pregna-4,20(Z)-diene-21-carboxylic acid γ-lactone (E/Z)-3-(Hydroxyimino)-6,6-(1,2-ethanediyl)-17β-hydroxy-19-nor-17α-pregna-4,20(Z)-diene-21-carboxylic acid γ-lactone (E/Z)-3-(Hydroxyimino)-17β-hydroxy-6α,7α-methylene-19-nor-17α-pregna-4,20(Z)-diene-21-carboxylic acid γ-lactone
(E/Z)-3-(Hydroxyimino)-17β-hydroxy-6β,7β-methylene-19-nor-17α-pregna-4,20(Z)-diene-21-carboxylic acid γ-lactone (E/Z)-3-(Hydroxyimino)-17β-hydroxy-19-nor-17α-pregna-4,6,20(Z)-triene-21-carboxylic acid γ-lactone (E/Z)-3-(Hydroxyimino)-16,16-(1,2-ethanediyl)-17β-hydroxy-19-nor-17α-pregna-4,20(Z)-diene-21-carboxylic acid γ-lactone -continued

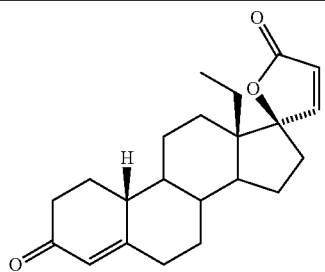

17β-Hydroxy-18-methyl-19-nor-17α-pregna-4,20(Z)-dien-3-one-21-carboxylic acid γ-lactone (Example 6)

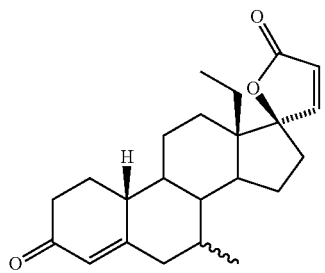 [SMILES: CC[C@]12CCC3C(C(C)CC4=CC(=O)CC[C@@H]43)C1CC[C@@]21C=CC(=O)O1]

17β-Hydroxy-7α,18-dimethyl-19-nor-17α-pregna-4,20(Z)-dien-3-one-21-carboxylic acid γ-lactone (Example 8A)

17β-Hydroxy-7β,18-dimethyl-19α-nor-17α-pregna-4,20(Z)-dien-3-one-21-carboxylic acid γ-lactone (Example 8B)

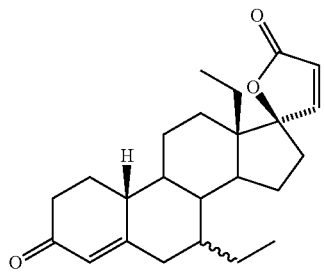 [SMILES: CCC1CC2=CC(=O)CC[C@@H]2C2CC[C@@]3(CC)C(CC[C@@]34C=CC(=O)O4)C12]

17β-Hydroxy-7α-ethyl-18-methyl-19-nor-17α-pregna-4,20(Z)-dien-3-one-21-carboxylic acid γ-lactone (Example 9A)

17β-Hydroxy-7β-ethy-18-methyl-19-nor-17α-pregna-4,20(Z)-dien-3-one-21-carboxylic acid γ-lactone (Example 9B)

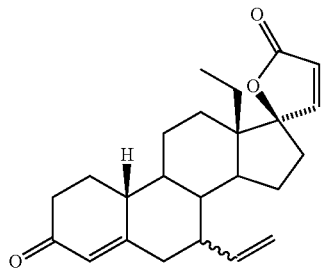 [SMILES: C=CC1CC2=CC(=O)CC[C@@H]2C2CC[C@@]3(CC)C(CC[C@@]34C=CC(=O)O4)C12]

17β-Hydroxy-7α-vinyl-18-methy-19-nor-17α-pregna-4,20(Z)-dien-3-one-21-carboxylic acid γ-lactone (Example 10A)

17β-Hydroxy-7β-vinyl-18-methy-19-nor-17α-pregna-4,20(Z)-dien-3-one-21-carboxylic acid γ-lactone (Example 10B)

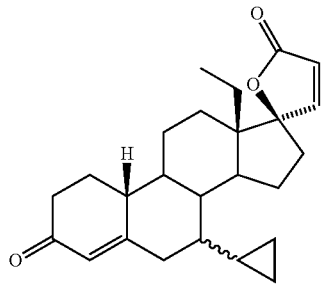 [SMILES: CC[C@]12CCC3C(C(C4CC4)CC4=CC(=O)CC[C@@H]43)C1CC[C@@]21C=CC(=O)O1]

17β-Hydroxy-7α-cyclopropyl-18-methyl-19-nor-17α-pregna-4,20(Z)-dien-3-one-21-carboxylic acid γ-lactone (Example 11A)

17β-Hydroxy-7β-cyclopropyl-18-methy-19-nor-17α-pregna-4,20(Z)-dien-3-one-21-carboxylic acid γ-lactone (Example 11B)

-continued

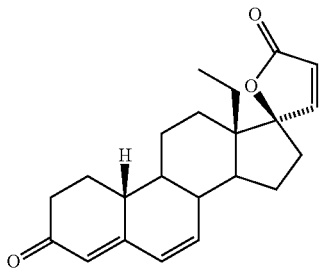 [SMILES: CC[C@]12CCC3C(C=CC4=CC(=O)CC[C@@H]43)C1CC[C@@]21C=CC(=O)O1]

17β-Hydroxy-18-methyl-19-nor-17α-pregna-4,6,20(Z)-trien-3-one-21-carboxylic acid γ-lactone

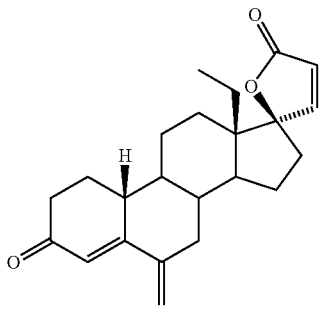 [SMILES: C=C1CC2C(CC[C@@]3(CC)C2CC[C@@]32C=CC(=O)O2)[C@H]2CCC(=O)C=C12]

17β-Hydroxy-18-methyl-6-methylene-19-nor-17α-pregna-4,20(Z)-dien-3-one-21-carboxylic acid γ-lactone

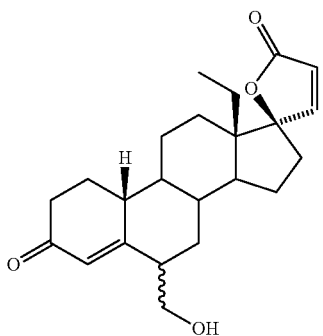 [SMILES: CC[C@]12CCC3C(CC(CO)C4=CC(=O)CC[C@@H]43)C1CC[C@@]21C=CC(=O)O1]

17β-Hydroxy-6α-hydroxymethylene-18-methyl-19-nor-17α-pregna-4,20(Z)-dien-3-one-21-carboxylic acid γ-lactone 17β-Hydroxy-6β-hydroxymethylene-18-methyl-19-nor-17α-pregna-4,20(Z)-dien-3-one-21-carboxylic acid γ-lactone (Example 15)

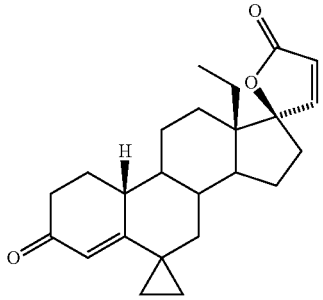 [SMILES: CC[C@]12CCC3C(CC4(CC4)C4=CC(=O)CC[C@@H]43)C1CC[C@@]21C=CC(=O)O1]

6,6-(1,2-Ethanediyl)-17β-hydroxy-18-methyl-19-nor-17α-pregna-4,20(Z)-dien-3-one-21-carboxylic acid γ-lactone (Example 16)

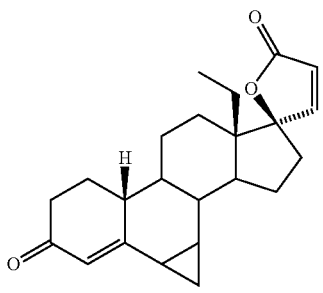 [SMILES: CC[C@]12CCC3C(C4CC4C4=CC(=O)CC[C@@H]43)C1CC[C@@]21C=CC(=O)O1]

17β-Hydroxy-18-methyl-6α,7α-methylene-19-nor-17α-pregna-4,20(Z)-dien-3-one-21-carboxylic acid γ-lactone (Example 19B)
17β-Hydroxy-18-methyl-6β,7β-methylene-19-nor-17α-pregna-4,20(Z)-dien-3-one-21-carboxylic acid γ-lactone (Example 19A)

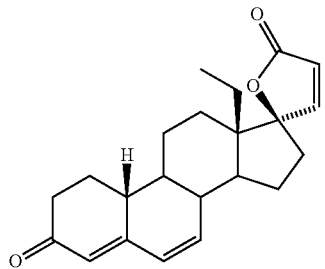 [SMILES: CC[C@]12CCC3C(C=CC4=CC(=O)CC[C@@H]43)C1CC[C@@]21C=CC(=O)O1]

17β-Hydroxy-18-methyl-19-nor-17α-pregna-4,6,20(Z)-trien-3-one-21-carboxylic acid γ-lactone (Example 7)

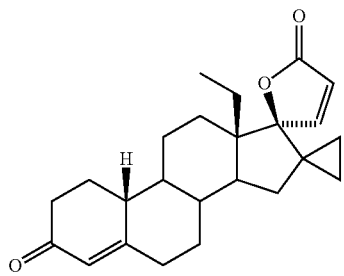 [SMILES: CC[C@]12CCC3C(CCC4=CC(=O)CC[C@@H]43)C1CC1(CC1)[C@@]21C=CC(=O)O1]

16,16-(1,2-Ethanediyl)-17β-hydroxy-18-methyl-19-nor-17α-pregna-4,20(Z)-dien-3-one-21-carboxylic acid γ-lactone

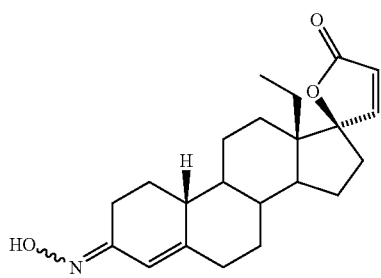 [SMILES: CC[C@]12CCC3C(CCC4=CC(=NO)CC[C@@H]43)C1CC[C@@]21C=CC(=O)O1]

(E/Z)-3-(Hydroxyimino)-17β-hydroxy-18-methyl-19-nor-17α-pregna-4,20(Z)-diene-21-carboxylic acid γ-lactone

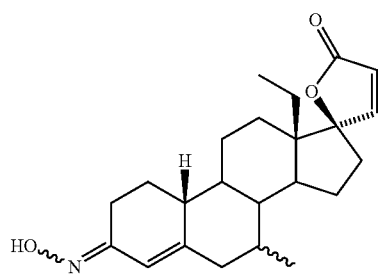 [SMILES: CC[C@]12CCC3C(C(C)CC4=CC(=NO)CC[C@@H]43)C1CC[C@@]21C=CC(=O)O1]

(E/Z)-3-(Hydroxyimino)-17β-hydroxy-7α,18-dimethyl-19-nor-17α-pregna-4,20(Z)-diene-21-carboxylic acid γ-lactone (E/Z)-3-(Hydroxyimino)-17β-hydroxy-7β,18-dimethyl-19-nor-17α-pregna-4,20(Z)-diene-21-carboxylic acid γ-lactone (E/Z)-3-(Hydroxyimino)-17β-hydroxy-7α-ethyl-18-methyl-19-nor-17α-pregna-4,20(Z)-diene-21-carboxylic acid γ-lactone

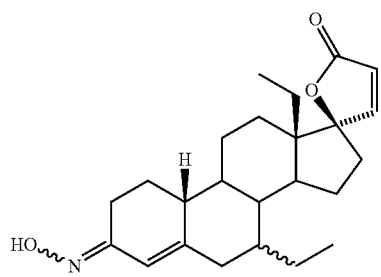 [SMILES: CCC1CC2=CC(=NO)CC[C@@H]2C2CC[C@@]3(CC)C(CC[C@@]34C=CC(=O)O4)C12]

(E/Z)-3-(Hydroxyimino)-17β-hydroxy-7β-ethyl-18-methyl-19-nor-17α-pregna-4,20(Z)-diene-21-carboxylic acid γ-lactone

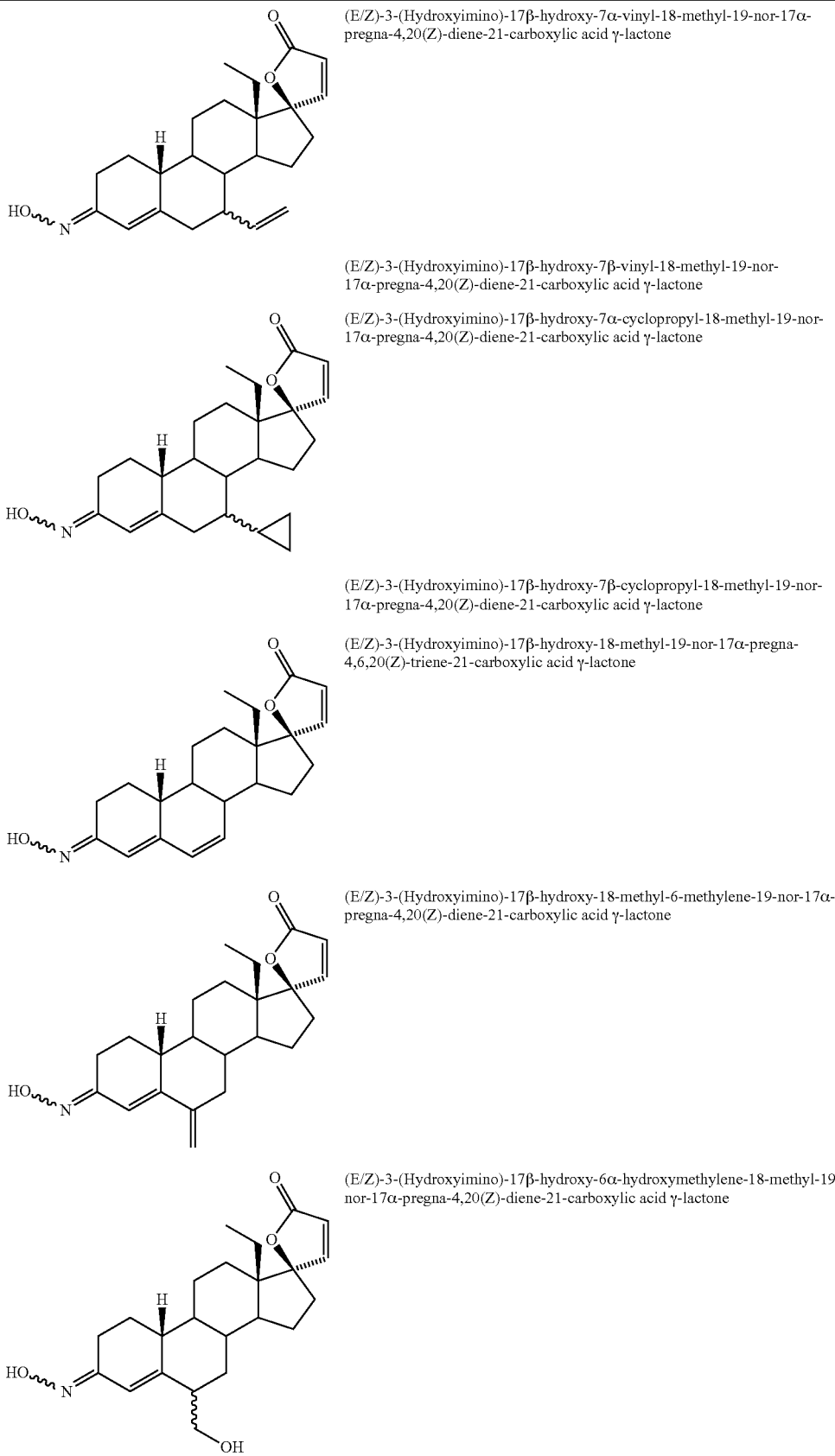

(E/Z)-3-(Hydroxyimino)-17β-hydroxy-7α-vinyl-18-methyl-19-nor-17α-pregna-4,20(Z)-diene-21-carboxylic acid γ-lactone (E/Z)-3-(Hydroxyimino)-17β-hydroxy-7β-vinyl-18-methyl-19-nor-17α-pregna-4,20(Z)-diene-21-carboxylic acid γ-lactone (E/Z)-3-(Hydroxyimino)-17β-hydroxy-7α-cyclopropyl-18-methyl-19-nor-17α-pregna-4,20(Z)-diene-21-carboxylic acid γ-lactone (E/Z)-3-(Hydroxyimino)-17β-hydroxy-7β-cyclopropyl-18-methyl-19-nor-17α-pregna-4,20(Z)-diene-21-carboxylic acid γ-lactone (E/Z)-3-(Hydroxyimino)-17β-hydroxy-18-methyl-19-nor-17α-pregna-4,6,20(Z)-triene-21-carboxylic acid γ-lactone (E/Z)-3-(Hydroxyimino)-17β-hydroxy-18-methyl-6-methylene-19-nor-17α-pregna-4,20(Z)-diene-21-carboxylic acid γ-lactone (E/Z)-3-(Hydroxyimino)-17β-hydroxy-6α-hydroxymethylene-18-methyl-19-nor-17α-pregna-4,20(Z)-diene-21-carboxylic acid γ-lactone

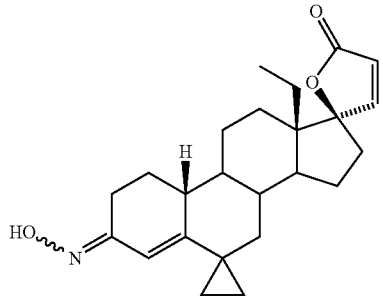 [SMILES: CC[C@]12CCC3C(CC4(CC4)C4=CC(=NO)CC[C@@H]43)C1CC[C@@]21C=CC(=O)O1]

(E/Z)-3-(Hydroxyimino)-17β-hydroxy-6β-hydroxymethylene-18-methyl-19-nor-17α-pregna-4,20(Z)-diene-21-carboxylic acid γ-lactone (E/Z)-3-(Hydroxyimino)-6,6-(1,2-ethanediyl)-17β-hydroxy-18-methyl-19-nor-17α-pregna-4,20(Z)-diene-21-carboxylic acid γ-lactone

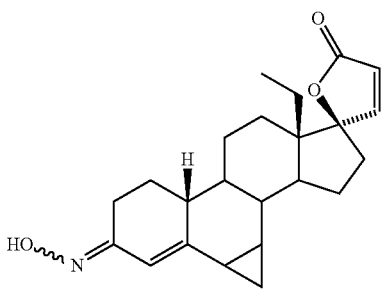 [SMILES: CC[C@]12CCC3C(C4CC4C4=CC(=NO)CC[C@@H]43)C1CC[C@@]21C=CC(=O)O1]

(E/Z)-3-(Hydroxyimino)-17β-hydroxy-18-methyl-6α,7α-methylene-19-nor-17α-pregna-4,20(Z)-diene-21-carboxylic acid γ-lactone
(E/Z)-3-(Hydroxyimino)-17β-hydroxy-18-methyl-6β,7β-methylene-19-nor-17α-pregna-4,20(Z)-diene-21-carboxylic acid γ-lactone

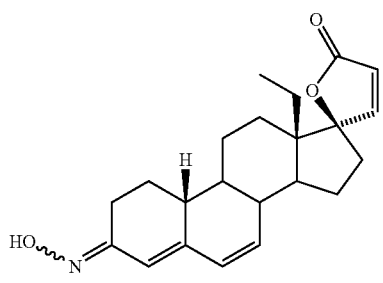 [SMILES: CC[C@]12CCC3C(C=CC4=CC(=NO)CC[C@@H]43)C1CC[C@@]21C=CC(=O)O1]

(E/Z)-3-(Hydroxyimino)-17β-hydroxy-18-methyl-19-nor-17α-pregna-4,6,20(Z)-triene-21-carboxylic acid γ-lactone

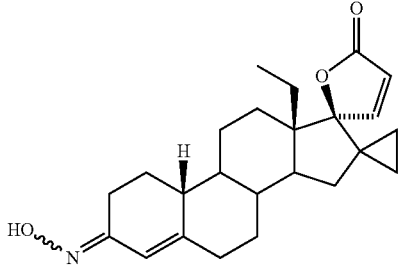 [SMILES: CC[C@]12CCC3C(CCC4=CC(=NO)CC[C@@H]43)C1CC1(CC1)[C@@]21C=CC(=O)O1]

(E/Z)-3-(Hydroxyimino)-16,16-(1,2-ethanediyl)-17β-hydroxy-18-methyl-19-nor-17α-pregna-4,20(Z)-diene-21-carboxylic acid γ-lactone 4-Chloro-17β-hydroxy-18-methyl-19-nor-17α-pregna-4,20(Z)-dien-3-one-21-carboxylic acid γ-lactone (Example 13)
4-Chloro-17β-hydroxy-19-nor-17α-pregna-4,20(Z)-dien-3-one-21-carboxylic acid γ-lactone (Example 14)

On the basis of their progestational efficacy, the novel compounds with the general chemical formula I can be used alone or in combination with estrogen in medicinal products for contraception.

The derivatives according to the invention are therefore suitable in particular for the production of a medicinal product for oral contraception and for the treatment of pre-, peri- and postmenopausal complaints, including use in preparations for hormone replacement therapy (HRT).

Owing to their favorable action profile, the derivatives according to the invention are moreover especially well suited to the treatment of premenstrual complaints, such as headaches, depressive moods, water retention and mastodynia.

The use of the derivatives according to the invention is especially preferred for the production of a medicinal product with progestational, and preferably also antimineralocorticoid and neutral to slightly androgenic action.

Treatment with the derivatives according to the invention is preferably applied to humans, but can also be carried out on related mammalian species, for example dog and cat.

For use of the derivatives according to the invention as medicinal products, they are combined with at least one suitable pharmaceutically harmless additive, for example a carrier. The additive is for example suitable for parenteral, preferably oral, application. Relevant materials are pharmaceutically suitable organic or inorganic inert additives, for example water, gelatin, gum arabic, lactose, starch, magnesium stearate, talc, vegetable oils, polyalkylene glycols etc. The medicinal products can be in solid form, for example as tablets, coated tablets, suppositories, capsules, or in liquid form, for example as solutions, suspensions or emulsions. Optionally they also contain excipients, such as preservatives, stabilizers, wetting agents or emulsifiers, salts for altering the osmotic pressure or buffers. For parenteral application, oily solutions are suitable in particular, for example solutions in sesame oil, castor oil and cottonseed oil are suitable. To increase the solubility, solubilizers can be added, for example benzyl benzoate or benzyl alcohol. It is also possible to incorporate the derivatives according to the invention in a transdermal system and therefore apply them transdermally. For oral application, consideration may be given in particular to tablets, coated tablets, capsules, pills, suspensions or solutions.

Further examples of administration routes are intravaginal or intrauterine administration. This is possible with physiologically tolerated solutions such as, for example, an aqueous or oily solution with or without suitable solubilizers, dispersants or emulsifiers. Examples of suitable oils are peanut oil, cottonseed oil, castor oil or sesame oil. The selection is by no means restricted thereto.

For intravaginal or intrauterine administration it is possible to use special systems such as an intravaginal system (e.g. vaginal ring, VRS) or an intrauterine system (IUS) which release an active substance of the present invention from a reservoir over a prolonged period (e.g. 1, 2, 3, 4 or 5 years).

A representative example of an intrauterine system which may be mentioned is MIRENA®. This is a T-shaped, levonorgestrel-releasing intrauterine system from Bayer Schering Pharma AG.

Administration is further possible via an implanted depot system composed of an inert carrier material such as, for example, a biodegradable polymer or a synthetic silicone polymer. These depot systems release the active ingredient in a controlled manner over a prolonged period (e.g. 3 months to 3 years) and are implanted subcutaneously.

The dosage of the derivatives according to the invention in contraceptive preparations should be 0.01 to 10 mg per day. The daily dose in the treatment of premenstrual complaints is around 0.1 to 20 mg. The progestational derivatives according to the invention in contraceptive preparations and in medicinal products for the treatment of premenstrual complaints are preferably administered orally. The daily dose is preferably administered as a single dose. The aforementioned dosages relate to oral administration forms.

On use of a depot formulation, the appropriate dosage, equivalent to the aforementioned oral dosages, is released continuously each day from the depot systems described above and employed in the long term.

A depot formulation, for example an IUS, releases per day an amount of 0.005 to 10 mg of a compound of general formula 1.

The progestational and estrogenic active components are preferably applied together orally in contraceptive preparations. The daily dose is preferably administered as a single dose.

As estrogens, consideration may be given to synthetic estrogens, preferably ethinylestradiol, but also mestranol, and natural estrogens, including phytoestrogens.

The estrogen is administered in a daily amount that corresponds to the pharmacological action of 0.01 to 0.04 mg ethinylestradiol. This amount relates to an oral administration form. If a different administration route is chosen, an appropriate dosage amount equivalent to the aforementioned oral dosage is to be used.

As estrogens in medicinal products for the treatment of pre-, peri- and postmenopausal complaints and for hormone replacement therapy, natural estrogens are mainly used, in particular estradiol, but also the esters of estradiol, for example estradiol valerate, or also conjugated estrogens (CEEs=conjugated equine estrogens).

The progestational, antimineralocorticoid and androgenic or antiandrogenic action of the compounds according to the invention was investigated by the following methods:

1. Progesterone Receptor Binding Test:

Using cytosol from progesterone receptor-expressing insect cells (Hi5), competitive binding to the progesterone receptor was determined from the ability to displace $^3$H-progesterone as reference substance from the receptor. If a compound has an affinity corresponding to progesterone, this corresponds to a competition factor (CF) of 1. CF values greater than 1 are characterized by a lower affinity for the progesterone receptor, and CF values of less than 1 are characterized by higher affinity.

2. Mineralocorticoid Receptor Binding Test:

The test was carried out as in 1., with the following modifications: cytosol from mineralocorticoid receptor-expressing insect cells (Hi5) was used, and the reference substance was $^3$H-aldosterone.

3. Androgen Receptor Binding Test:

The test was carried out as in 1., with the following modifications: cytosol from androgen receptor-expressing insect cells (Hi5) was used, and the reference substance was $^3$H-testosterone.

The results of the binding tests and the ratio of the competition factors CF(PR) and CR(MR) are shown in Table 1, which for comparison also shows receptor binding values of drospirenone as reference substance A.

4. Determination of Progestational Action by Means of Transactivation Tests:

The culture medium used for culture of the cells used for the assay was DMEM (Dulbecco's Modified Eagle Medium: 4500 mg/ml glucose; PAA, #E15-009) with 10% FCS (Biochrom, S0115, batch #615B), 4 mM L-glutamine, 1% penicillin/streptomycin, 1 mg/ml G418 and 0.5 µg/ml puromycin.

Reporter cell lines (CHO K1 cells stably transfected with a fusion protein from the PR-ligand-binding domain and a Gal4-transactivation domain and a reporter construct, which contained luciferase under the control of a Gal4-responsive promoter) were seeded at a density of $4\times10^4$ cells per well in white, opaque tissue culture plates each with 96 wells (PerkinElmer, #P12-106-017) and kept in culture medium with 3% DCC-FCS (serum treated with activated charcoal to remove interfering components contained in the serum). The test compounds were added eight hours later, and the cells were incubated with the compounds for 16 hours. The tests were carried out in triplicate. At the end of incubation the medium containing the effector was removed and replaced with lysis buffer. After luciferase assay substrate (Promega, #E1501) had been added, the 96-well plates were then put in a microplate luminometer (Pherastar, BMG Labtech), and the luminescence was measured. The $IC_{50}$ values were evaluated using software for calculating dose-effect relations. Table 2 presents the test results and, for comparison, corresponding results for drospirenone as reference substance A.

5. Determination of Antimineralocorticoid Action by Means of Transactivation Tests:

The antimineralocorticoid activity of the test substances was determined as for the transactivation tests described above.

The following modifications were undertaken: In this case reporter cell lines were used (MDCK cells) that express the human mineralocorticoid receptor, and transiently contain a reporter construct that contains luciferase under the control of a steroid hormone-responsive promoter.

The culture medium used for cultivation of the cells used for the assay was DMEM EARLE'S MEM (PAA, Cat.: E15-025) provided with 1000 penicillin/0.1 mg/ml streptomycin (PAA, Cat: P11-010), 4 mM L-glutamine (PAA, Cat: M11-004) and fetal calf serum (BIO Witthaker, Cat: DE14-801F).

For determination of antimineralocorticoid efficacy, 1 nM aldosterone (SIGMA A-6628, Lot 22H4033) was added to the cells, to achieve almost maximum stimulation of the reporter gene. Inhibition of the effect indicated a mineralocorticoid-antagonistic action of the substances (Table 2; for comparison, corresponding values for drospirenone (A)).

6. Determination of Androgenic/Antiandrogenic Action by Means of Transactivation Tests:

The androgenic/antiandrogenic action of the test substances was determined as for the transactivation tests described above.

The following modifications were made: In this case reporter cell lines were used (PC3 cells) that express the androgen receptor, and a reporter construct that contains luciferase under the control of a steroid hormone-responsive promoter.

The culture medium used for cultivation of the cells used for the assay was RPMI medium without phenol red (PAA, #E15-49), provided with 100 U penicillin/0.1 mg/ml streptomycin (PAA, Cat: P11-010), 4 mM L-glutamine (PAA, Cat: M11-004) and fetal calf serum (BIO Witthaker, Cat: DE14-801F).

For determination of the antiandrogenic efficacy, 0.05 nM R1881 was added to the cells, in order to achieve almost maximum stimulation of the reporter gene. Inhibition of the effect indicated an androgen-antagonistic action of the substances (Table 2; for comparison, corresponding values for drospirenone (A)).

If the production of the starting compounds is not described here, these are known to a person skilled in the art or can be prepared similarly to known compounds or methods described here. The isomeric mixtures can be separated into the individual compounds by the usual methods, for example crystallization, chromatography or salt formation. The salts are prepared in the usual way, by adding, to a solution of the compound with the general chemical formula I, the equivalent amount or an excess of a base or acid, which is optionally in solution, if necessary separating the precipitate or processing the solution in the usual way.

The compounds with the general chemical formula I are prepared, starting from compounds with the general chemical formula 1a (Scheme 2) or 1b (Scheme 3), by the method presented in Scheme 1, in which $R^4$, $R^{6a}$, $R^{6b}$, $R^7$, $R^{15}$, $R^{18}$ and Z have the meanings stated previously, with the proviso that $R^6$, $R^7$ in the compound with the general chemical formula 8b together form oxygen or methylene, and in which $R^{16a}$, $R^{16b}$ in the compounds with the general chemical formulae 32a and 40a together form methylene,
in the compounds with the general chemical formulae 32b and 40b together form 1,2-ethanediyl and
in the compounds with the general chemical formulae 32c and 40c are, independently of one another, hydrogen, $C_1$-$C_{10}$-alkyl, U is an oxygen atom, two alkoxy groups $OR^{19}$ or a $C_2$-$C_{10}$-alkylene-α,ω-dioxy group, which can be linear or branched, and $R^{19}$ stands for a $C_1$-$C_{20}$-alkyl residue, $R^{20}$ is a $C_1$-$C_{20}$-alkyl residue, X is an $NR^{21a}R^{21b}$ group or an alkoxy group $OR^{22}$, $R^{21a}$, $R^{21b}$ independently of one another, are hydrogen, $C_{10}$-$C_{10}$-alkyl or together form a $C_4$-$C_{10}$-α,ω-alkylene group, which can be linear or branched, and $R^{22}$ is a $C_1$-$C_{20}$-alkyl residue.

For a person skilled in the art it is obvious that in the descriptions of the synthetic transformations it is always assumed that if necessary other functional groups present on the steroid structure are suitably protected.

The introduction of a 6,7-double bond with formation of compounds with the general chemical formulae 5, 8a, 10 or 12 is carried out by bromination of the respective 3,5-dienol ethers 4, 7, 9 or 11 followed by elimination of hydrogen bromide (see for example J. Fried, J. A. Edwards, *Organic Reactions in Steroid Chemistry*, from Nostrand Reinhold Company 1972, p. 265-374).

The dienol ether bromination of compounds 4, 7, 9 or 11 can be carried out for example as in the specification from *Steroids* 1, 233 (1963). Elimination of hydrogen bromide with formation of the compounds with the general chemical formulae 5, 8a, 10 or 12 is achieved by heating the 6-bromo compound with basic reagents, for example LiBr or $Li_2CO_3$, in aprotic solvents, such as dimethylformamide, at temperatures of 50-120° C. or alternatively by heating the 6-bromo compounds in a solvent, such as collidine or lutidine.

The introduction of a substituent $R^4$ can be carried out for example, starting from a compound with one of the general chemical formulae 3, 5, 6, 8a, 8b or 10 by epoxidation of the 4,5-double bond with hydrogen peroxide in alkaline conditions and reaction of the resultant epoxide in a suitable solvent with acids with the general chemical formula H—$R^4$, where $R^4$ can be a halogen atom, preferably chlorine or bromine. Compounds in which $R^4$ denotes bromine can, for example, be reacted with 2,2-difluoro-2-(fluorosulfonyl)methyl acetate in dimethylformamide in the presence of copper(I) iodide to compounds in which $R^4$ denotes fluorine. Alternatively, starting from a compound with one of the general chemical formulae 3, 5, 6, 8a, 8b or 10, halogen can be introduced directly by reaction with sulfuryl chloride or sulfuryl bromide in the presence a suitable base, for example pyridine, with $R^4$ denoting chlorine or bromine.

Compound 5 or 12 is transformed by methenylation of the 6,7-double bond by known methods, for example with dimethylsulfoxonium methylide (see for example DE-A 11 83 500, DE-A 29 22 500, EP-A 0 019 690, U.S. Pat. No. 4,291,029; *J. Am. Chem. Soc.* 84, 867 (1962)) to a compound 8b or 13 ($R^6$, $R^7$ together form a methylene group), obtaining a mixture of the α- and β-isomers, which can be separated for example by chromatography into the individual isomers.

Compounds of type 8b or 13 can be obtained as described in the examples or similarly to these specifications, using reagents that are similar to those described there.

The synthesis of the spirocyclic compound 10 ($R^{6a}$, $R^{6b}$ together form 1,2-ethanediyl) starts from compounds 3 or 6, which are first converted to a 3-amino-3,5-diene derivative 7 ($X=NR^{21a}R^{21b}$). By reaction with formalin in alcoholic solution, the 6-hydroxymethylene derivative 8a ($R^6$=hydroxymethylene) is obtained. After converting the hydroxyl group into a leaving group, such as a mesylate, tosylate or even benzoate, compound 10 can be prepared by reaction with trimethylsulfoxonium iodide using bases, such as alkali hydroxides, alkali alcoholates, in suitable solvents, such as dimethyl sulfoxide.

In order to introduce a 6-methylene group, compound 8a ($R^6$=hydroxymethylene) can be dehydrated, for example with hydrochloric acid in dioxan/water. Once again, after converting the hydroxyl group into a leaving group, such as a mesylate, tosylate or even benzoate, compound 10 ($R^{6a}$, $R^{6b}$ together form methylene) can be obtained (see DE-A 34 02 329, EP-A 0 150 157, U.S. Pat. No. 4,584,288; *J. Med. Chem.* 34, 2464 (1991)).

Another possibility for the production of 6-methylene compounds 10 is the direct reaction of the 4(5) unsaturated 3-ketones, for example of compound 8a ($R^6$=hydrogen) with acetals of formaldehyde in the presence of sodium acetate with for example phosphoryl chloride or phosphorus pentachloride in suitable solvents, such as chloroform (see for example K. Annen, H. Hofmeister, H. Laurent and R. Wiechert, *Synthesis* 34 (1982)).

The 6-methylene compounds can be used for the preparation of compounds with the general chemical formula 10, in which $R^{6a}$ is methyl and $R^{6b}$ and $R^7$ together form an additional bond.

For this it is possible for example to use a method described in *Tetrahedron* 21, 1619 (1965), in which isomerization of the double bond is achieved by heating the 6-methylene compounds in ethanol with 5% palladium/charcoal catalyst, pretreated either with hydrogen or by heating with a small amount of cyclohexene. The isomerization can also be carried out with a catalyst that has not been pretreated, if a small amount of cyclohexene is added to the reaction mixture. The formation of small proportions of hydrogenated products can be prevented by adding an excess of sodium acetate.

Alternatively, compound 9 ($X=OR^{22}$) can be used as precursor. The direct preparation of 6-methyl-4,6-dien-3-one derivatives has been described (see K. Annen, H. Hofmeister, H. Laurent and R. Wiechert, *Lieb. Ann.* 712 (1983)).

Compounds 10 in which $R^{6b}$ represents an α-methyl function can be prepared in suitable conditions from the 6-methylene compounds (10: $R^{6a}$, $R^{6b}$ together form methylene) by hydrogenation. The best results (selective hydrogenation of the exo-methylene function) are achieved by transfer-hydrogenation (*J. Chem. Soc.* 3578 (1954)). If the 6-methylene derivatives 10 are heated in a suitable solvent, for example ethanol, in the presence a hydride donor, for example cyclohexene, then 6α-methyl derivatives are obtained at very good yields. Small proportions of 6β-methyl compound can be isomerized in acid conditions (*Tetrahedron* 1619 (1965)).

The selective preparation of 6β-methyl compounds is also possible. For this, the 4-en-3-ones, such as compound 8a, are reacted for example with ethylene glycol, trimethyl orthoformate in dichloromethane in the presence of catalytic amounts of an acid, for example p-toluenesulfonic acid, to the corresponding 3-ketals. During this ketalization there is isomerisation of the double bond into position $C^5$. Selective epoxidation of this 5-double bond is achieved for example by using organic per-acids, for example m-chloroperbenzoic acid, in a suitable solvent, such as dichloromethane. As an alternative, the epoxidation can also be carried out with hydrogen peroxide in the presence for example of hexachloroacetone or 3-nitrotrifluoroacetophenone. The 5,6α-epoxides formed can then be opened axially using appropriate alkylmagnesium halides or alkyllithium compounds. In this way, 5α-hydroxy-6β-alkyl compounds are obtained. The 3-keto protecting group can be cleaved, obtaining the 5α-hydroxy function, by treatment in mild acidic conditions (acetic acid or 4N hydrochloric acid at 0° C.). Basic elimination of the 5 α-hydroxy function with for example dilute aqueous sodium hydroxide solution yields the 3-keto-4-ene compounds with a 6-alkyl group in the β position. Alternatively, cleavage of the ketal in harsher conditions (with aqueous hydrochloric acid or another strong acid) yields the corresponding 6α-alkyl compounds.

The introduction of a 7-alkyl, 7-alkenyl or 7-alkynyl group to form compounds with the general chemical formula 6 is effected by 1,6-addition of a corresponding organometallic compound to the precursor with the general chemical formula 5 under the action of copper salts. Divalent metals, such as magnesium and zinc, are preferred; chlorine, bromine and iodine are preferred as counterions. Suitable copper salts are monovalent or divalent copper compounds, for example copper chloride, copper bromide or copper acetate. The reaction takes place in an inert solvent, for example tetrahydrofuran, diethyl ether or dichloromethane.

The compounds 3, 5, 6, 8a, 8b, 10, 11 or 12 obtained, in which Z stands for an oxygen atom, can be converted by reaction with hydroxylamine hydrochloride, alkyloxyamine hydrochlorides or sulfonyl hydrazines in the presence of a tertiary amine at temperatures from −20° C. to +40° C. to their corresponding E/Z-configured oximes or sulfonyl hydrazones (general chemical formula I with Z denoting $NOR^1$, $NNHSO_2R^1$)). Suitable tertiary bases are for example trimethylamine, triethylamine, pyridine, N,N-dimethylaminopyridine, 1,5-diazabicyclo[4.3.0]non-5-ene (DBN) and 1,5-diazabicyclo[5.4.0]undec-5-ene (DBU), pyridine being preferred. An analogous method is described for example in WO-A 98/24801 for the production of corresponding 3-oxyimino derivatives of drospirenone.

For the preparation of an end product with the general chemical formula I with Z denoting two hydrogen atoms, the 3-oxo group can be removed for example following the instructions given in DE-A 28 05 490 by reductive cleavage of a thioketal of the 3-keto compound on a suitable precursor, for example of compounds with one of the general chemical formulae 3, 5, 6, 8a, 8b, 10, 11 or 12.

The formation of spirolactones to compounds with one of the general chemical formulae 3 or 8b is carried out starting from the corresponding 17-hydroxypropenyl compounds 2 or 13, by oxidation. Oxidation processes that may be mentioned are for example the Jones oxidation, oxidation with potassium permanganate for example in an aqueous system of tert.-butanol and sodium dihydrogen phosphate, oxidation with sodium chlorite in aqueous tert.-butanol, optionally in the presence a chlorine trap, for example in the presence of 2-methyl-2-butene, or by oxidation with manganese dioxide.

Scheme 1
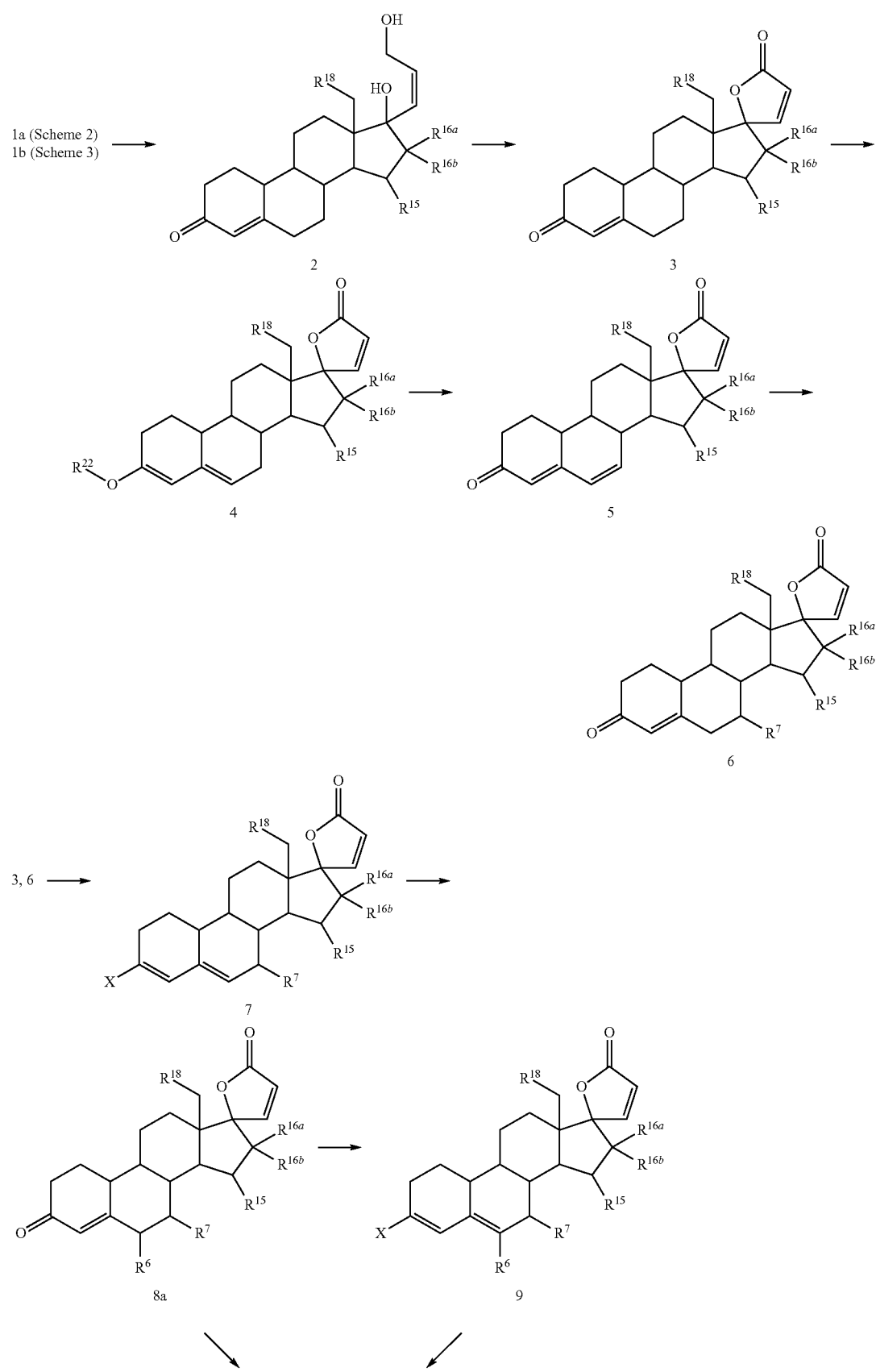

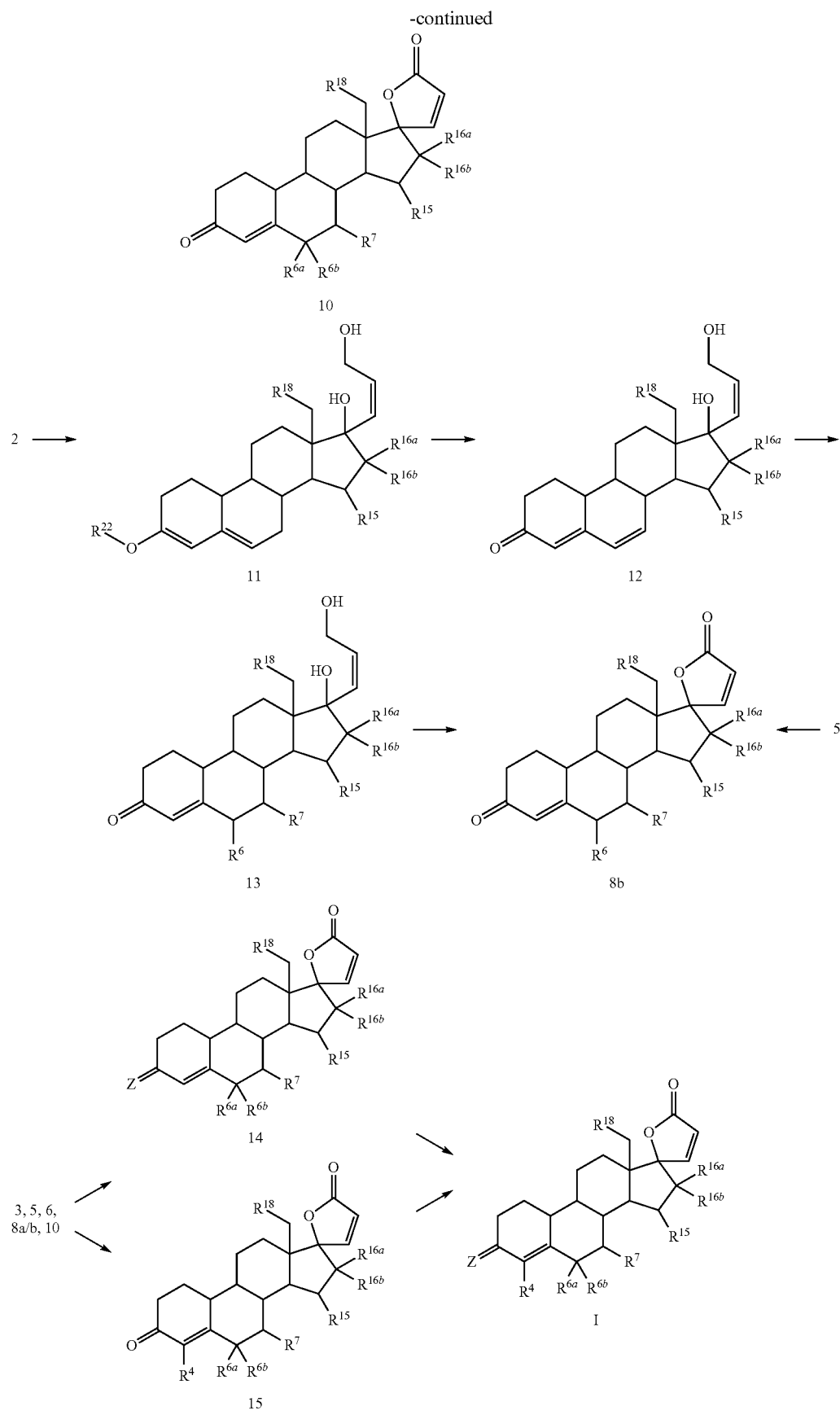

The compounds with the general chemical formula 1a are prepared by the method presented in Scheme 2, in which $R^{15}$ and $R^{18}$ have the meanings stated previously and $R^{16a}$, $R^{16b}$ in 32a together form methylene,
in 32b together form 1,2-ethanediyl and
in 32c independently of one another are hydrogen, $C_1$-$C_{10}$-alkyl and
$R^{20}$ is $C_1$-$C_{20}$-alkyl.

Compounds 30 to 1a in Scheme 2 each have a double bond between $C^5$ and $C^6$ or between $C^5$ and $C^{10}$ and another double bond between $C^2$ and $C^3$ or between $C^3$ and $C^4$.

The compounds with the general chemical formula 1b are prepared by the method presented in Scheme 3, in which $R^{15}$ and $R^{18}$ have the meanings stated previously and $R^{16a}$, $R^{16b}$ in 40a together form methylene,
in 40b together form 1,2-ethanediyl and
in 40c independently of one another are hydrogen, $C_1$-$C_{10}$-alkyl,
U is an oxygen atom, two alkoxy groups $OR^{19}$, a $C_2$-$C_{10}$-alkylene-α,ω-dioxy group, which can be linear or branched, and
$R^{19}$ stands for a $C_1$-$C_{20}$-alkyl residue.

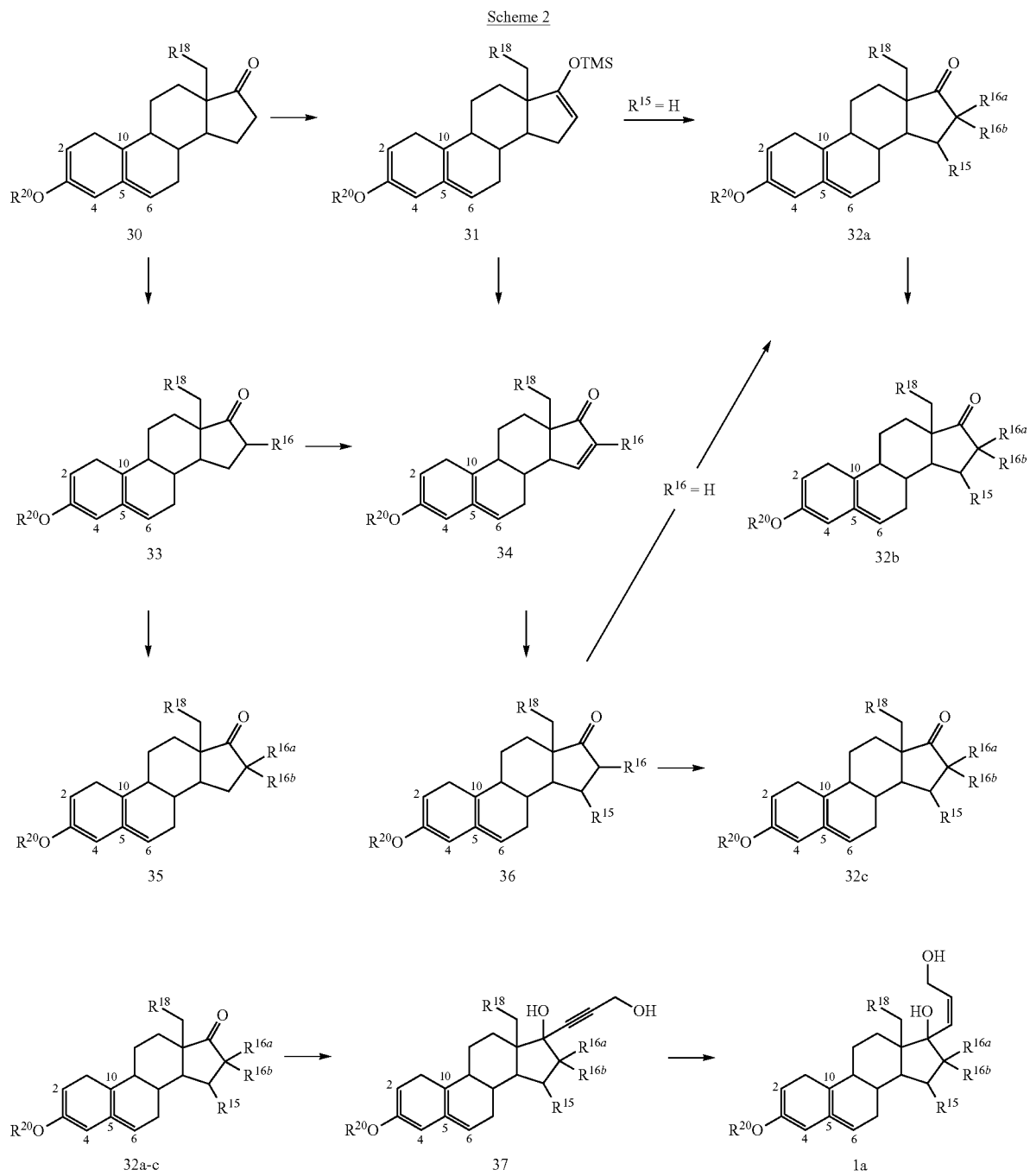

Scheme 2

Compounds 38 to 1b in Scheme 3 each have a double bond between $C^4$ and $C^5$ or between $C^5$ and $C^6$ or between $C^5$ and $C^{10}$.
Scheme 3
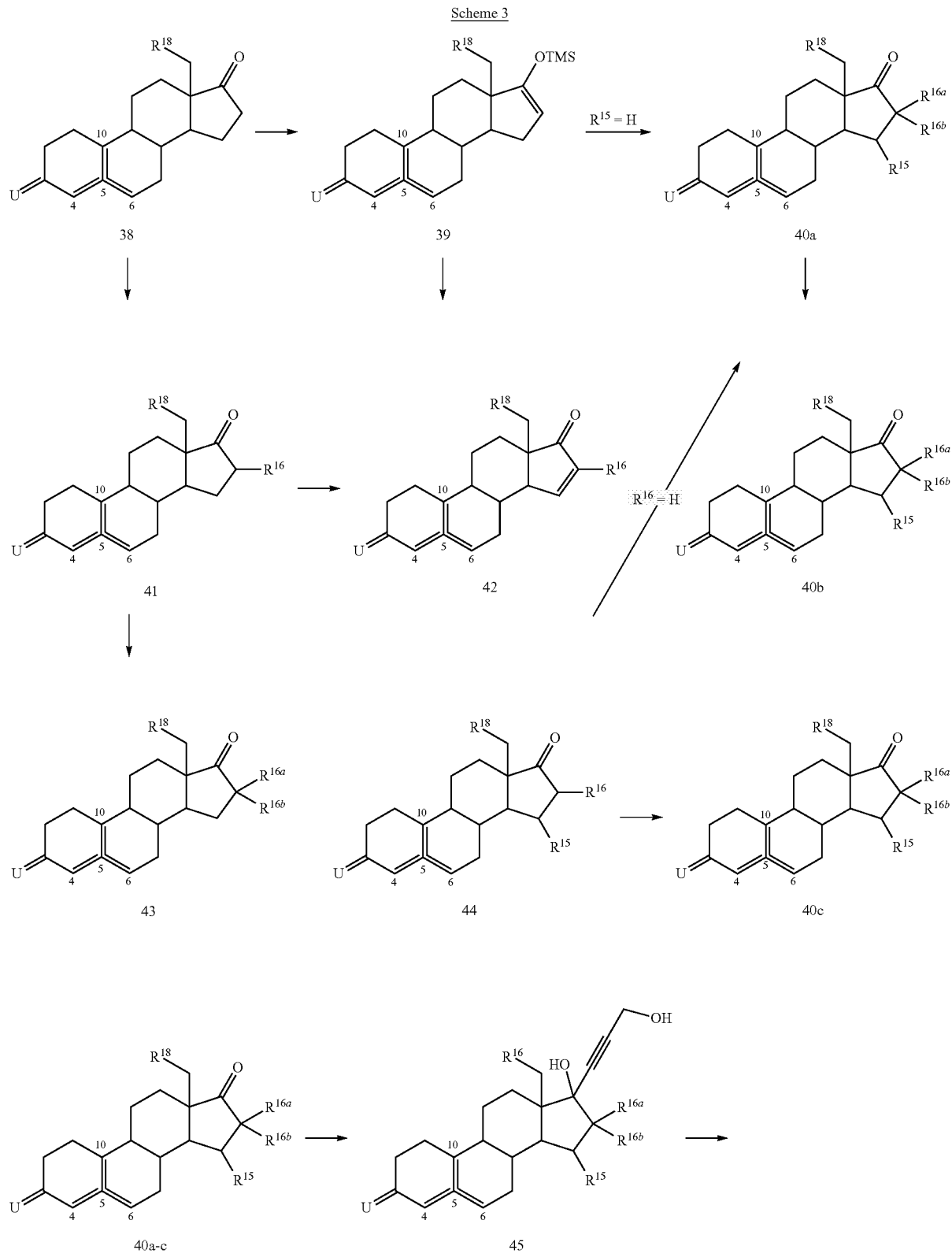

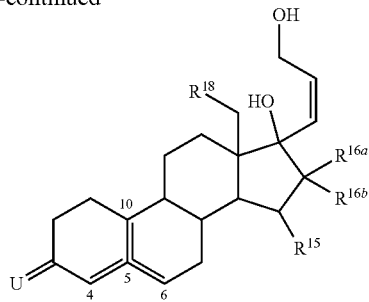

1b

The following examples are provided for further explanation of the invention, without it being limited to the examples shown:

EXAMPLE 1

Dienone Formation from Dienol Ether

17β-Hydroxy-19-nor-17α-pregna-4,6,20(Z)-trien-3-one-21-carboxylic acid γ-lactone 448 mg sodium acetate, 4.5 ml water and, in portions, a total of 1.73 g dibromohydantoin were added, at −10° C., to a solution of 4.12 g of the compound prepared according to Example 1a in 44.8 ml N-methylpyrrolidone. After 30 minutes, 1.68 g lithium bromide and 1.48 g lithium carbonate were added and the mixture was heated for 1 hour to a bath temperature of 100° C. The mixture was poured into a mixture of ice and sodium chloride solution, and the precipitated product was filtered off with suction. 3.83 g of the title compound was isolated as raw product, which was reacted further directly or was further purified by recrystallization.

$^1$H-NMR (CDCl$_3$): δ=1.01-1.17 (2H), 1.12 (3H), 1.33 (1H), 1.46-1.62 (3H), 1.70 (1H), 1.81 (1H), 1.91-2.07 (2H), 2.22-2.41 (5H), 2.55 (1H), 5.80 (1H), 5.97 (1H), 6.17 (1H), 6.24 (1H), 7.42 (1H) ppm.

EXAMPLE 1A

Dienol Ether Formation

17β-Hydroxy-3-methoxy-19-nor-17α-pregna-3,5,20(Z)-triene-21-carboxylic acid γ-lactone 695 mg pyridinium-p-toluenesulfonate was added to a solution of 6.02 g of the compound prepared according to Example 1b in 68.7 ml 2,2-dimethoxypropane and heated under reflux for 2 hours. The mixture was poured into saturated sodium hydrogencarbonate solution, extracted several times with ethyl acetate, the combined organic extracts were washed with saturated sodium chloride solution, and the product was dried over sodium sulfate. The residue obtained after filtration and removal of the solvent was purified by recrystallization. 4.12 g of the title compound was isolated.

EXAMPLE 1B 17-spirolactonization with Manganese Dioxide

17β-Hydroxy-19-nor-17α-pregna-4,20(Z)-dien-3-one-21-carboxylic acid γ-lactone 2.03 g manganese dioxide was added to a solution of 269 mg of the compound prepared according to Example 1c in 21 ml dichloromethane, and the mixture was stirred at 23° C. for approx. 5 hours. It was then filtered on Celite and, after concentration by evaporation and chromatography, 211 mg of the title compound was isolated as a crystalline solid.

$^1$H-NMR (CDCl$_3$): δ=0.84 (1H), 0.97-1.17 (2H), 1.10 (3H), 1.27 (1H), 1.34-1.67 (5H), 1.78-1.98 (4H), 2.11 (1H), 2.20-2.45 (5H), 2.50 (1H), 5.84 (1H), 5.96 (1H), 7.43 (1H) ppm.

EXAMPLE 1C 3-ketal Cleavage

17α(Z)-(3'-Hydroxypropen-1'-yl)-17β-hydroxyestra-4-en-3-one 1.51 ml of 4N hydrochloric acid was added to a solution of 367 mg of the compound prepared according to Example 1d in 30 ml acetone, and the mixture was stirred for 30 minutes at 23° C. Then it was poured into saturated sodium hydrogencarbonate solution, extracted several times with ethyl acetate, the combined organic extracts were washed with saturated sodium chloride solution, and the product was dried over sodium sulfate. The residue obtained after filtration and removal of the solvent was purified by chromatography. 269 mg of the title compound was isolated.

EXAMPLE 1D

Lindlar Hydrogenation

17α(Z)-(3'-Hydroxypropen-1'-yl)-3,3-dimethoxy-17β-hydroxyestra-5(10)-ene 5.35 ml pyridine and 560 mg palladium on barium sulfate were added to a solution of 3.94 g of the compound prepared according to Example 1e in 90 ml tetrahydrofuran, and the mixture was hydrogenated under a hydrogen atmosphere. The mixture was filtered on Celite, and after concentration by evaporation and chromatography, 3.04 g of the title compound was isolated.

EXAMPLE 1E

Hydroxypropyne Addition

17α-(3'-Hydroxypropyn-1'-yl)-3,3-dimethoxy-17β-hydroxyestra-5(10)-ene 1.13 l of 2.5 molar solution of butyllithium in hexane was added to a solution of 92.7 ml of 2-propyn-1-ol in 1.4 l tetrahydrofuran at −60° C. After 30 minutes, a solution of 100 g of 3,3-dimethoxy-estra-5(10)-en-17-one in 0.8 l tetrahydrofuran was added dropwise, the mixture was heated to 23° C. and stirred for a further 16 hours. Then the mixture was poured into water, extracted several times with ethyl acetate, the combined organic extracts were washed with saturated sodium chloride solution and dried over sodium sulfate. The residue obtained after filtration and removal of the solvent was purified by crystallization. 72.9 g of the title compound was isolated.

EXAMPLE 2

1,6-Addition

17β-Hydroxy-7α-methyl-19-nor-17α-pregna-4,20(Z)-dien-3-one-21-carboxylic acid γ-lactone (A) and
17β-Hydroxy-7β-methyl-19-nor-17α-pregna-4,20(Z)-dien-3-one-21-carboxylic acid γ-lactone (B)

193 µl of 3 molar solution of methyl magnesium chloride in tetrahydrofuran was added dropwise to a suspension of 4.6 mg copper(I) chloride in 0.7 ml tetrahydrofuran cooled to −30° C., and it was stirred for a further 10 minutes. The solution was cooled to −25° C. and was added dropwise to 75 mg of the compound prepared according to Example 1 in 2 ml tetrahydrofuran. After 1 minute it was poured into 1N hydrochloric acid, extracted several times with ethyl acetate, the combined organic extracts were washed with saturated sodium chloride solution and dried over sodium sulfate. The residue obtained after filtration and removal of the solvent was purified by chromatography. 23.4 mg of the title compound A was isolated along with a still contaminated mixture, which contained proportions of the title compound B.
$^1$H-NMR (CDCl$_3$) of A: δ=0.85 (3H), 0.98-1.38 (4H), 1.15 (3H), 1.45-2.46 (14H), 2.52 (1H), 5.89 (1H), 6.00 (1H), 7.50 (1H) ppm.

EXAMPLE 3

17β-Hydroxy-7α-ethyl-19-nor-17α-pregna-4,20(Z)-dien-3-one-21-carboxylic acid γ-lactone (A) and
17β-Hydroxy-7β-ethyl-19-nor-17α-pregna-4,20(Z)-dien-3-one-21-carboxylic acid γ-lactone (B)

Similarly to Example 2, 100 mg of the compound prepared according to Example 1 was reacted using ethyl magnesium chloride, and after processing and purification, 19 mg of the title compound A was isolated along with a still contaminated mixture, which contained proportions of the title compound B.
$^1$H-NMR (CDCl$_3$) of A: δ=0.9 (3H), 0.94-1.16 (3H), 1.11 (3H), 1.18-1.37 (2H), 1.44-1.98 (9H), 2.06 (1H), 2.21-2.45 (5H), 2.58 (1H), 5.86 (1H), 5.96 (1H), 7.45 (1H) ppm.

EXAMPLE 4

17β-Hydroxy-7α-vinyl-19-nor-17α-pregna-4,20(Z)-dien-3-one-21-carboxylic acid γ-lactone (A) and
17β-Hydroxy-7β-vinyl-19-nor-17α-pregna-4,20(Z)-dien-3-one-21-carboxylic acid γ-lactone (B)

Similarly to Example 2, 700 mg of the compound prepared according to Example 1 was reacted using vinylmagnesium chloride, and after processing and purification, 46 mg of the title compound A was isolated along with a still contaminated mixture, which contained proportions of the title compound B.
$^1$H-NMR (cD$_2$Cl$_2$) of A: δ=1.03 (1H), 1.13 (3H), 1.16-1.36 (2H), 1.42-1.66 (4H), 1.76 (1H), 1.84-1.99 (3H), 2.10-2.68 (8H), 5.14 (1H), 5.18 (1H), 5.74-5.87 (2H), 5.94 (1H), 7.47 (1H) ppm.

EXAMPLE 5

16,16-(1,2-Ethanediyl)-17β-hydroxy-19-nor-17α-pregna-4,20(Z)-dien-3-one-21-carboxylic acid γ-lactone 400 mg of the compound prepared according to Example 5a was reacted similarly to Example 1b, and after processing and purification, 358 mg of the title compound was isolated.
$^1$H-NMR (CDCl$_3$): δ=0.11 (1H), 0.44 (1H), 0.54 (1H), 0.89 (1H), 1.03 (1H), 1.06-1.17 (2H), 1.23 (3H), 1.31 (1H), 1.46-1.63 (4H), 1.72-1.89 (4H), 2.12 (1H), 2.22-2.34 (3H), 2.41 (1H), 2.50 (1H), 5.84 (1H), 5.88 (1H), 7.40 (1H) ppm.

EXAMPLE 5A 16,16-(1,2-Ethanediyl)-17α(Z)-(3'-hydroxypropen-1'-yl)-17β-hydroxyestra-4-en-3-one 2.83 g of the compound prepared according to Example 5b was reacted similarly to Example 1c, and after processing and purification, 1.64 g of the title compound was isolated.

EXAMPLE 5B 3,3-Dimethoxy-16,16-(1,2-ethanediyl)-17α(Z)-(3'-hydroxypropen-1'-yl)-17β-hydroxyestra-5(10)-ene 2.98 g of the compound prepared according to Example 5c was reacted similarly to Example 1d, and after processing, 2.84 g of the title compound was isolated, and was reacted further without purification.

EXAMPLE 5C 3,3-Dimethoxy-16,16-(1,2-ethanediyl)-17α(Z)-(3'-hydroxypropyn-1'-yl)-17β-hydroxyestra-5(10)-ene 100 mg of the compound prepared according to Example 5d was reacted similarly to Example 1e, and after processing and purification, 116 mg of the title compound was isolated, and was reacted further without purification.

EXAMPLE 5D 16,16-cyclopropanation from 16-methylene 3,3-Dimethoxy-16,16-(1,2-ethanediyl)-estra-5(10)-en-17-one 1.05 g of a 60% suspension of sodium hydride in white oil was added in portions at 23° C. to a solution of 5.61 g sulfoxonium iodide in 100 ml dimethylsulfoxide. It was stirred for a further 2 hours, a solution of 2.1 g of the compound prepared according to Example 5e in 40 ml dimethylsulfoxide was then added dropwise, and the solution was left to react for a further 16 hours. The mixture was poured into water, extracted several times with ethyl acetate, the combined organic extracts were washed with saturated sodium chloride solution and dried over sodium sulfate. 2.52 g of the title compound was isolated, which still contained residual amounts of white oil and was reacted further without additional purification.

EXAMPLE 5E 16,16-methylene from Silylenol Ether 3,3-Dimethoxy-16-methylene-estra-5(10)-en-17-one 10 ml of N,N,N',N'-tetramethyldiaminomethane was added to a solution of 6.1 g of 3,3-dimethoxy-17-trimethylsilyloxy-estra-5(10)16-diene in 30 ml tetrahydrofuran, cooled to 3° C. and 10 ml acetic anhydride was added. The mixture was heated to 23° C. and left to react for 2 days. Then it was poured into saturated sodium hydrogencarbonate solution, extracted several times with ethyl acetate, the combined organic extracts were washed with saturated sodium chloride solution and dried over sodium sulfate. The product was purified by silica-gel chromatography; 1.6 g of the title compound was isolated.

EXAMPLE 6

17β-Hydroxy-18-methyl-19-nor-17α-pregna-4,20 (Z)-dien-3-one-21-carboxylic acid γ-lactone 10 g of the compound prepared according to Example 6a was reacted similarly to Example 1b, and after processing and purification, 9.3 g of the title compound was isolated.

$^1$H-NMR (CDCl$_3$): δ=0.77-0.90 (2H), 0.99 (3H), 1.02-1.18 (2H), 1.40-1.71 (6H), 1.74-1.99 (5H), 2.11 (1H), 2.20-2.44 (5H), 2.51 (1H), 5.84 (1H), 5.96 (1H), 7.44 (1H) ppm.

EXAMPLE 6A

17α(Z)-(3'-Hydroxypropen-1'-yl)-18-methyl-17β-hydroxyestra-4-en-3-one 6.35 g of the compound prepared according to Example 6b was reacted similarly to Example 1c, and after processing and purification, 3.02 g of the title compound was isolated.

EXAMPLE 6B

17α(Z)-(3'-Hydroxypropen-1'-yl)-3-methoxy-18-methyl-17β-hydroxyestra-2,5(10)-diene 7.86 g of the compound prepared according to Example 6c was reacted similarly to Example 1d, and after processing, 6.35 g of the title compound was isolated, and was reacted further without purification.

EXAMPLE 6C

17α(Z)-(3'-Hydroxypropyn-1'-yl)-3-methoxy-18-methyl-17β-hydroxyestra-2,5(10)-diene 5.0 g of 3-methoxy-18-methyl-17β-hydroxyestra-2,5(10)-dien-17-one was reacted similarly to Example 1e, and after processing, 7.86 g of the title compound was isolated, and was reacted further without purification.

EXAMPLE 7

17β-Hydroxy-18-methyl-19-nor-17α-pregna-4,6,20 (Z)-trien-3-one-21-carboxylic acid γ-lactone 9.0 g of the compound prepared according to Example 7a was reacted similarly to Example 1, and after processing and purification, 5.04 g of the title compound was isolated.

$^1$H-NMR (CDCl$_3$): δ=0.93 (1H), 1.06 (3H), 1.16 (2H), 1.50-1.92 (7H), 1.96-2.10 (2H), 2.25-2.49 (5H), 2.59 (1H), 5.84 (1H), 6.03 (1H), 6.23 (1H), 6.29 (1H), 7.47 (1H) ppm.

EXAMPLE 7A

17β-Hydroxy-3-methoxy-18-methyl-19-nor-17α-pregna-3,5,20(Z)-triene-21-carboxylic acid γ-lactone 10.0 g of the compound prepared according to Example 1b was reacted similarly to Example 1a, and after processing, 10.9 g of the title compound was isolated, and was reacted further without purification.

EXAMPLE 8

17β-Hydroxy-7α,18-dimethyl-19-nor-17α-pregna-4,20(Z)-dien-3-one-21-carboxylic acid γ-lactone (A) and 17β-Hydroxy-7β,18-dimethyl-19-nor-17α-pregna-4,20(Z)-dien-3-one-21-carboxylic acid γ-lactone (B)

Similarly to Example 2, 200 mg of the compound prepared according to Example 7 was reacted using methyl magnesium chloride, and after processing and purification, 115 mg of the title compound A was isolated along with a still contaminated mixture, which contained proportions of the title compound B.

$^1$H-NMR (CDCl$_3$) of A: δ=0.82 (4H), 1.00 (3H), 1.02-1.13 (2H), 1.49-1.61 (3H), 1.67 (2H), 1.71-1.81 (3H), 1.86 (1H), 1.95 (1H), 1.99-2.09 (2H), 2.22-2.45 (5H), 2.51 (1H), 5.85 (1H), 5.96 (1H), 7.45 (1H) ppm.

EXAMPLE 9

17β-Hydroxy-7α-ethyl-18-methyl-19-nor-17α-pregna-4,20(Z)-dien-3-one-21-carboxylic acid γ-lactone (A) and 17β-Hydroxy-7β-ethyl-18-methyl-19-nor-17α-pregna-4,20(Z)-dien-3-one-21-carboxylic acid γ-lactone (B)

Similarly to Example 2, 200 mg of the compound prepared according to Example 7 was reacted using ethyl magnesium chloride, and after processing and purification, 91 mg of the title compound A was isolated along with a still contaminated mixture, which contained proportions of the title compound B.

$^1$H-NMR (CDCl$_3$) of A: δ=0.81 (1H), 0.90 (3H), 1.00 (3H), 1.02-1.11 (3H), 1.33 (1H), 1.47-1.89 (10H), 1.94 (1H), 2.06 (1H), 2.22-2.44 (5H), 2.59 (1H), 5.85 (1H), 5.96 (1H), 7.45 (1H) ppm.

EXAMPLE 10

17β-Hydroxy-7α-vinyl-18-methyl-19-nor-17α-pregna-4,20(Z)-dien-3-one-21-carboxylic acid γ-lactone (A) and 17β-Hydroxy-7β-vinyl-18-methyl-19-nor-17α-pregna-4,20(Z)-dien-3-one-21-carboxylic acid γ-lactone (B)

Similarly to Example 2, 200 mg of the compound prepared according to Example 7 was reacted using vinylmagnesium chloride, and after processing and purification, 74 mg of the title compound A was isolated along with a still contaminated mixture, which contained proportions of the title compound B.

$^1$H-NMR (CDCl$_3$) of A: δ=0.80 (1H), 1.00 (3H), 1.05 (1H), 1.15 (1H), 1.44-1.60 (4H), 1.66 (2H), 1.73-1.95 (5H), 2.24-2.36 (3H), 2.41-2.48 (2H), 2.52-2.60 (2H), 5.11 (1H), 5.13 (1H), 5.74 (1H), 5.86 (1H), 5.95 (1H), 7.42 (1H) ppm.

EXAMPLE 11

17β-Hydroxy-7α-cyclopropyl-18-methyl-19-nor-17α-pregna-4,20(Z)-dien-3-one-21-carboxylic acid γ-lactone (A) and 17β-Hydroxy-7β-cyclopropyl-18-methyl-19-nor-17α-pregna-4,20(Z)-dien-3-one-21-carboxylic acid γ-lactone (B)

Similarly to Example 2, 200 mg of the compound prepared according to Example 7 was reacted using cyclopropylmagnesium bromide, and after processing and purification, 38 mg of the title compound A was isolated along with a still contaminated mixture, which contained proportions of the title compound B.

$^1$H-NMR (CDCl$_3$) of A: δ=−0.03 (1H), 0.31 (1H), 0.42-0.59 (3H), 0.85 (1H), 0.99 (3H), 1.04 (1H), 1.13 (1H), 1.33 (1H), 1.49-1.68 (4H), 1.74-2.00 (6H), 2.11 (1H), 2.22-2.46 (5H), 2.51 (1H), 5.89 (1H), 5.97 (1H) 7.47 (1H) ppm.

EXAMPLE 12

17β-Hydroxy-7α-cyclopropyl-19-nor-17α-pregna-4,20(Z)-dien-3-one-21-carboxylic acid γ-lactone (A) and 17β-Hydroxy-7β-cyclopropyl-19-nor-17α-pregna-4,20(Z)-dien-3-one-21-carboxylic acid γ-lactone (B)

Similarly to Example 2, 300 mg of the compound prepared according to Example 1 was reacted using cyclopropylmagnesium chloride, and after processing and purification, 89 mg of the title compound A was isolated along with a still contaminated mixture, which contained proportions of the title compound B.

$^1$H-NMR (CDCl$_3$) of A: δ=−0.02 (1H), 0.31 (1H), 0.47 (1H), 0.5-0.57 (2H), 1.04 (1H), 1.10 (3H), 1.13 (1H), 1.24-1.36 (2H), 1.47-1.59 (3H), 1.74 (1H), 1.80-1.97 (4H), 2.11 (1H), 2.25-2.33 (3H), 2.38-2.45 (2H), 2.51 (1H), 5.89 (1H), 5.97 (1H), 7.47 (1H) ppm.

EXAMPLE 13

4-chlorination

4-Chloro-17β-hydroxy-18-methyl-19-nor-17α-pregna-4,20(Z)-dien-3-one-21-carboxylic acid γ-lactone 20 μl sulfuryl chloride was added at 3° C. to a solution of 50 mg of the compound prepared according to Example 6 in 0.5 ml pyridine and was stirred for a further 1.5 hours at 3° C. The solution was poured into saturated sodium hydrogencarbonate solution, extracted several times with ethyl acetate, the combined organic extracts were washed with saturated sodium chloride solution and dried over sodium sulfate. The residue obtained after filtration and removal of the solvent was purified by chromatography. 14 mg of the title compound was isolated.

$^1$H-NMR (CDCl$_3$): δ=0.81-0.96 (2H), 0.99 (3H), 1.02-1.20 (2H), 1.44 (1H), 1.52-1.72 (5H), 1.76-1.86 (3H), 1.91-2.00 (2H), 2.12 (1H), 2.21-2.45 (4H), 2.64 (1H), 3.38 (1H), 5.97 (1H), 7.43 (1H) ppm.

EXAMPLE 14

4-Chloro-17β-hydroxy-19-nor-17α-pregna-4,20(Z)-dien-3-one-21-carboxylic acid γ-lactone Similarly to Example 13, 100 mg of the compound prepared according to Example 1b was reacted, and after processing and purification, 77.8 mg of the title compound was isolated.

$^1$H-NMR (CDCl$_3$): δ=0.84-1.67 (10H), 1.10 (3H), 1.78-2.01 (4H), 2.11 (1H), 2.20-2.47 (4H), 2.63 (1H), 5.96 (1H), 7.43 (1H) ppm.

EXAMPLE 15

Introduction of 6-hydroxymethyl

17β-Hydroxy-6β-hydroxymethylene-18-methyl-19-nor-17α-pregna-4,20(Z)-dien-3-one-21-carboxylic acid γ-lactone 427 μl of a 37% aqueous formaldehyde solution was added to a solution of 427 mg of the compound prepared according to Example 15a in a mixture of 4 ml toluene and 9 ml ethanol and stirred for 6 hours at 23° C. The solution was concentrated by evaporation, and the residue was purified by chromatography. 23.4 mg of the title compound was isolated.

$^1$H-NMR (CDCl$_3$): δ=0.78-0.91 (2H), 0.99 (3H), 1.05 (1H), 1.30-1.85 (12H), 1.90-1.99 (2H), 2.17-2.48 (5H), 2.67 (1H), 3.71 (2H), 5.93 (1H), 5.96 (1H), 7.44 (1H) ppm.

EXAMPLE 15A

Dienamine Formation

17β-Hydroxy-3-pyrrolidinyl-18-methyl-19-nor-17α-pregna-3,5,20(Z)-triene-21-carboxylic acid γ-lactone 280 μl pyrrolidine was added to a solution of 500 mg of the compound prepared according to Example 1b in 5 ml methanol and heated under reflux for 2 hours. The mixture was cooled, the precipitate was filtered off with suction, washed again with a little cold methanol, and 434 mg of the title compound was obtained, and was reacted further without additional purification.

EXAMPLE 16

6-spirocyclopropanation 6,6-(1,2-Ethanediyl)-17β-hydroxy-18-methyl-19-nor-17α-pregna-4,20(Z)-dien-3-one-21-carboxylic acid γ-lactone 235 mg trimethylsulfoxonium iodide was dissolved in 1.7 ml dimethylsulfoxide, 43 mg of a 60% sodium hydride dispersion was added, and the mixture was stirred for 2 hours at 23° C. Then a solution of 140 mg of the compound prepared according to Example 16a in . . . (?) ml dimethylsulfoxide was added dropwise and the mixture was stirred for a further 2 hours at 23° C. The mixture was poured into water, extracted several times with ethyl acetate, the combined organic extracts were washed with water and saturated sodium chloride solution and dried over sodium sulfate. The residue obtained after filtration and removal of the solvent was purified by chromatography. 38.2 mg of the title compound was isolated.

$^1$H-NMR (CDCl$_3$): δ=0.41 (1H), 0.56 (1H), 0.70 (1H), 0.82-1.18 (4H), 1.01 (3H), 1.26 (1H), 1.38-1.99 (11H), 2.13-2.47 (5H), 5.69 (1H), 5.96 (1H), 7.43 (1H) ppm.

EXAMPLE 16A 6-tosyloxymethyl formation

17β-Hydroxy-6β-(p-tolylsulfonyloxymethyl)-18-methyl-19-nor-17α-pregna-4,20(Z)-dien-3-one-21-carboxylic acid γ-lactone 1.5 ml triethylamine and 514 mg p-toluenesulfonic acid chloride were added to a solution of 400 mg of the compound prepared according to Example 15 in 15 ml dichloromethane and stirred for 15 hours at 23° C. The mixture was poured into saturated sodium carbonate solution, extracted several times with ethyl acetate, the combined organic extracts were washed with water and saturated sodium chloride solution and dried over sodium sulfate. The residue obtained after filtration and removal of the solvent was purified by chromatography. 145 mg of the title compound was isolated.

EXAMPLE 17

17β-Hydroxy-6β-hydroxymethylene-19-nor-17α-pregna-4,20(Z)-dien-3-one-21-carboxylic acid γ-lactone Similarly to Example 15, 517 mg of the compound prepared according to Example 17a was reacted, and after processing and purification, 156 mg of the title compound was isolated.

$^1$H-NMR (CDCl$_3$): δ=0.84 (1H), 0.97-1.12 (2H), 1.09 (3H), 1.20-2.36 (15H), 2.44 (1H), 2.66 (1H), 3.70 (2H), 5.93 (1H), 5.96 (1H), 7.43 (1H) ppm.

EXAMPLE 17A

17β-Hydroxy-3-pyrrolidinyl-19-nor-17α-pregna-3,5,20(Z)-triene-21-carboxylic acid γ-lactone Similarly to Example 15a, 840 mg of the compound prepared according to Example 1b was reacted, and after processing and purification, 524 mg of the title compound was isolated.

EXAMPLE 18

6,6-(1,2-Ethanediyl)-17β-hydroxy-19-nor-17α-pregna-4,20(Z)-dien-3-one-21-carboxylic acid γ-lactone Similarly to Example 16, 80 mg of the compound prepared according to Example 18a was reacted, and after processing and purification, 26 mg of the title compound was isolated.

$^1$H-NMR (CDCl$_3$): δ=0.42 (1H), 0.55 (1H), 0.70 (1H), 0.86-1.10 (3H), 1.12 (3H), 1.21-1.97 (11H), 2.15-2.46 (5H), 5.69 (1H), 5.96 (1H), 7.43 (1H) ppm.

EXAMPLE 18A

17β-Hydroxy-6β-(p-tolylsulfonyloxymethyl)-19-nor-17α-pregna-4,20(Z)-dien-3-one-21-carboxylic acid γ-lactone Similarly to Example 16a, 540 mg of the compound prepared according to Example 17 was reacted, and after processing and purification, 80 mg of the title compound was isolated.

EXAMPLE 19

Corey Cyclopropanation

17β-Hydroxy-18-methyl-6β,7β-methylene-19-nor-17α-pregna-4,20(Z)-dien-3-one-21-carboxylic acid γ-lactone (A) and 17β-Hydroxy-18-methyl-6α,7α-methylene-19-nor-17α-pregna-4,20(Z)-dien-3-one-21-carboxylic acid γ-lactone (B)

Similarly to Example 16, 1.5 g of the compound prepared according to Example 7 was reacted, and after processing and purification, 188 mg of the title compound A and 430 mg of the title compound B were isolated.

$^1$H-NMR (CDCl$_3$) of A: δ=0.58 (1H), 0.82-1.07 (3H), 1.02 (3H), 1.24-1.38 (2H), 1.43-2.09 (12H), 2.16-2.52 (4H), 6.02 (1H), 6.16 (1H), 7.50 (1H) ppm.

$^1$H-NMR (CDCl$_3$) of B: δ=0.71-1.09 (5H), 1.03 (3H), 1.37-1.53 (2H), 1.56-2.46 (14H), 2.55 (1H), 6.01 (1H), 6.08 (1H), 7.52 (1H) ppm.

EXAMPLE 20

17β-Hydroxy-6β,7β-methylene-19-nor-17α-pregna-4,20(Z)-dien-3-one-21-carboxylic acid γ-lactone (A) and 17β-Hydroxy-6α,7α-methylene-19-nor-17α-pregna-4,20(Z)-dien-3-one-21-carboxylic acid γ-lactone (B)

Similarly to Example 16, 1.28 g of the compound prepared according to Example 1 was reacted, and after processing and purification, 66 mg of the title compound A and 112 mg of the title compound B were isolated.

$^1$H-NMR (CDCl$_3$) of A: δ=0.58 (1H), 0.89-1.58 (9H), 1.12 (3H), 1.68-2.11 (6H), 2.22 (1H), 2.29-2.52 (3H), 6.02 (1H), 6.15 (1H), 7.50 (1H) ppm.

$^1$H-NMR (CDCl$_3$) of B: δ=0.73 (1H), 0.81 (1H), 0.96 (1H), 1.06 (1H), 1.17 (3H), 1.19 (1H), 1.37-2.12 (11H), 2.19 (1H), 2.27-2.42 (2H), 2.55 (1H), 6.01 (1H), 6.08 (1H), 7.51 (1H) ppm.

EXAMPLE 21

Inert depot systems amenable to intrauterine implantation and composed of a biodegradable polymer or a synthetic silicone polymer consisting of an active ingredient-containing core in the appropriate polymer-active ingredient mixing ratio, surrounded by a polymer membrane ensuring the desired daily release rate, are introduced into the lumen of the rat uterus. The female animals are castrated beforehand and pretreated with estradiol for three days. The implants of different length (5-20 mm) and a restricted diameter (1.1 to 2 mm) remain for between 4 and 14 days in the rat uterus in order to investigate the local and systemic progestational effect of the released active ingredient on the basis of various parameters in different tissues. The following parameters are measured: 1) local progestational effect on the uterus on the basis of the weight of the uterus, the histologically detectable epithelial height and the expression of progestogen-regulated marker genes (e.g. IGFBP-1); 2) systemic progestational effect on the mammary gland on the basis of the expression of progestogen-regulated marker genes (e.g. RankL), 3) systemic progestational effect on the pituitary on the basis of the LH level (reduction in the estrogen-induced elevation of the LH level).

The compounds of the present invention show a significant progestational effect in the uterus which is comparable to a corresponding treatment with a levonorgestrel-containing depot system such as MIRENA®.

TABLE 1

| | | Receptor binding values | | | | | |
|---|---|---|---|---|---|---|---|
| | | Receptor binding | | | | | |
| | | Progesterone receptor (PR) | | Mineralocorticoid receptor (MR) | Androgen receptor | | |
| Ex. | Structure | IC50 [nM] | Competition factor | Competition factor | IC50 [nM] | Competition factor | CF PR/ CF MR |
| A | | 43.3 | 2.7 | 0.5 | 630 | 37 | 5.40 |
| 1 | | 230 | 11.41 | 33.0 | 10000 | 1000.0 | 0.35 |
| 2A | | 310 | 8.33 | 7.6 | 110 | 4.8 | 1.10 |
| 3A | | 1300 | 54.22 | 8.7 | 89 | 2.8 | 6.23 |

TABLE 1-continued

| | | Receptor binding values | | | | | |
|---|---|---|---|---|---|---|---|
| | | Receptor binding | | | | | |
| | | Progesterone receptor (PR) | | Mineralocorticoid receptor (MR) | Androgen receptor | | |
| Ex. | Structure | IC50 [nM] | Competition factor | Competition factor | IC50 [nM] | Competition factor | CF PR/ CF MR |
| 4A | (structure) | 760 | 27.47 | 18.7 | 130 | 4.7 | 1.47 |
| 5 | (structure) | 110 | 3.31 | 12.7 | 310 | 33.8 | 0.26 |
| 6 | (structure) | 45 | 3.07 | 2.4 | 28 | 3.4 | 1.28 |
| 7 | (structure) | 110 | 6.15 | 3.9 | 2600 | 112.0 | 1.58 |
| 8A | (structure) | 160 | 5.95 | 1.0 | 43 | 1.3 | 5.95 |

TABLE 1-continued

| | | Receptor binding values | | | | | |
|---|---|---|---|---|---|---|---|
| | | | Receptor binding | | | | |
| | | Progesterone receptor (PR) | | Mineralocorticoid receptor (MR) | Androgen receptor | | |
| Ex. | Structure | IC50 [nM] | Competition factor | Competition factor | IC50 [nM] | Competition factor | CF PR/ CF MR |
| 9A | | 670 | 25.12 | 1.6 | 76 | 2.3 | 15.70 |
| 9B | | | | | | | |
| 10A | | 450 | 18.90 | 5.1 | 50 | 1.8 | 3.71 |
| 11A | | 500 | 21.03 | 2.4 | 94 | 3.4 | 8.76 |

TABLE 1-continued

| | | Receptor binding values | | | | | |
|---|---|---|---|---|---|---|---|
| | | Receptor binding | | | | | |
| | | Progesterone receptor (PR) | | Mineralocorticoid receptor (MR) | Androgen receptor | | |
| Ex. | Structure | IC50 [nM] | Competition factor | Competition factor | IC50 [nM] | Competition factor | CF PR/ CF MR |
| 12A | | 2600 | 109.04 | 12.1 | 300 | 9.6 | 9.01 |
| 13 | | 750 | 28.06 | 47.0 | 170 | 8.3 | 0.60 |
| 14 | | 1200 | 53.06 | 39.0 | 140 | 7.5 | 1.36 |
| 15 | | 1000 | 1000.00 | 8.7 | 1000 | 1000.0 | PR inactive |

TABLE 1-continued

| | | Receptor binding values | | | | | |
|---|---|---|---|---|---|---|---|
| | | Receptor binding | | | | | |
| | | Progesterone receptor (PR) | | Mineralocorticoid receptor (MR) | Androgen receptor | | |
| Ex. | Structure | IC50 [nM] | Competition factor | Competition factor | IC50 [nM] | Competition factor | CF PR/ CF MR |
| 16 | | 49 | 2.29 | 1.2 | 42 | 1.8 | 1.91 |
| 17 | | 1000 | 1000.00 | 4.0 | 1000 | 1000.0 | inactive |
| 18 | | 44 | 1.45 | 1.9 | 37 | 1.9 | 0.76 |

TABLE 2

| | | In-vitro transactivation | | | | | | | |
|---|---|---|---|---|---|---|---|---|---|
| | | Progesterone receptor | | Mineralocorticoid receptor | | Androgen receptor | | | |
| Ex. | Structure | Agonism EC50 [nM] | Agonism efficacy [%] | Antagonism IC50 [nM] | Antagonism efficacy [%] | Agonism EC50 [nM] | Agonism efficacy [%] | Antagonism IC50 [nM] | Antagonism efficacy [%] |
| A | | 88 | 72.2 | 3.3 | 64.1 | 112.5 | 24.26 | 27 | 54.58 |
| 1 | | | | 870 | 93.2 | 130 | 44.27 | 1000 | 5 |
| 2A | | 220.0 | 44.4 | 180 | 129.8 | 16 | 64.09 | 1000 | 5 |
| 3A | | 780.0 | 16.2 | 360 | 55.9 | 25 | 30.25 | 11 | 41.26 |

TABLE 2-continued

| | | Values for in-vitro transactivation | | | | | | | |
|---|---|---|---|---|---|---|---|---|---|
| | | In-vitro transactivation | | | | | | | |
| | | Progesterone receptor | | Mineralocorticoid receptor | | Androgen receptor | | | |
| Ex. | Structure | Agonism EC50 [nM] | Agonism efficacy [%] | Antagonism IC50 [nM] | Antagonism efficacy [%] | Agonism EC50 [nM] | Agonism efficacy [%] | Antagonism IC50 [nM] | Antagonism efficacy [%] |
| 4A | | 140.0 | 67.5 | 28 | 120.0 | 13 | 53.6 | 1000 | 5 |
| 5 | | 13.0 | 46.9 | 840 | 73.1 | 140 | 37.8 | 1000 | 5 |
| 6 | | | | 12 | 109.6 | 53 | 59.8 | 19 | 33.8 |
| 7 | | inactive | | 100 | 94.2 | 1000 | 5 | 100 | 59.23 |

татBLE 2-continued

Values for in-vitro transactivation

| | | In-vitro transactivation | | | | | | | |
|---|---|---|---|---|---|---|---|---|---|
| | | Progesterone receptor | | Mineralocorticoid receptor | | Androgen receptor | | | |
| | | Agonism EC50 [nM] | Agonism efficacy [%] | Antag- onism IC50 [nM] | Antag- onism efficacy [%] | Agonism EC50 [nM] | Agonism efficacy [%] | Antag- onism IC50 [nM] | Antag- onism efficacy [%] |
| Ex. | Structure | | | | | | | | |
| 8A | | inactive | | 11 | 113.8 | 1.7 | 78.75 | 1000 | 5 |
| 9A | | inactive | | 130 | 97.6 | 5.1 | 63.33 | 1000 | 5 |
| 9B | | | | | | | | | |
| 10A | | 140.0 | 52.4 | 940 | 80.0 | 1.3 | 74.78 | 1000 | 5 |

TABLE 2-continued

Values for in-vitro transactivation

| Ex. | Structure | Progesterone receptor | | Mineralocorticoid receptor | | Androgen receptor | | | |
|---|---|---|---|---|---|---|---|---|---|
| | | Agonism EC50 [nM] | Agonism efficacy [%] | Antagonism IC50 [nM] | Antagonism efficacy [%] | Agonism EC50 [nM] | Agonism efficacy [%] | Antagonism IC50 [nM] | Antagonism efficacy [%] |
| 11A | 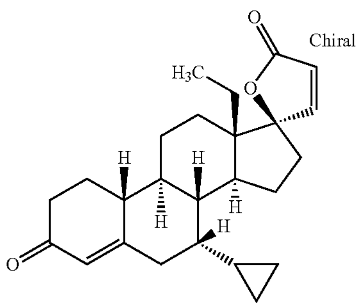 | 120.0 | 47.7 | 230 | 88.8 | 10 | 41.38 | 16 | 34.45 |
| 12A | 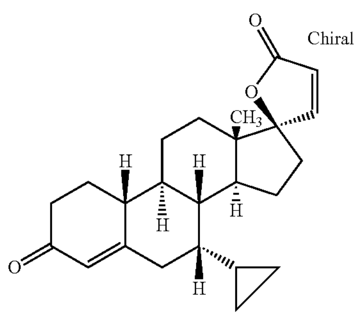 | inactive | | 110 | 116.9 | 67 | 21.13 | 48 | 69.75 |
| 13 | 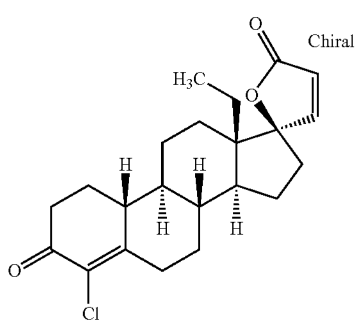 | 1000.0 | 25.3 | inactive | | 57 | 33.71 | 12 | 44.18 |
| 14 | 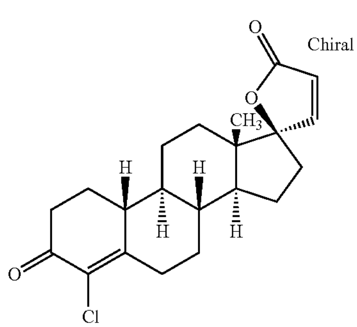 | inactive | | 700 | 21.6 | 100 | 22.74 | 70.5 | 63.26 |

ТABLE 2-continued

Values for in-vitro transactivation

| Ex. | Structure | Progesterone receptor | | Mineralocorticoid receptor | | Androgen receptor | | | |
|---|---|---|---|---|---|---|---|---|---|
| | | Agonism EC50 [nM] | Agonism efficacy [%] | Antagonism IC50 [nM] | Antagonism efficacy [%] | Agonism EC50 [nM] | Agonism efficacy [%] | Antagonism IC50 [nM] | Antagonism efficacy [%] |
| 15 | (structure) | inactive | | inactive | | 1000 | 5 | 1000 | 5 |
| 16 | (structure) | 9.7 | 38.4 | 75 | 107.9 | 1.1 | 91.19 | 1000 | 5 |
| 17 | (structure) | inactive | | inactive | | 1000 | 5 | 1000 | 5 |
| 18 | (structure) | 45.0 | 127.0 | 520 | 89.3 | 3.7 | 87.91 | 1000 | 5 |

The invention claimed is:

1. A 17-Hydroxy-19-nor-21-carboxylic acid-steroid γ-lactone selected from
    17β-Hydroxy-7α-vinyl-19-nor-17α-pregna-4,20(Z)-dien-3-one-21-carboxylic acid γ-lactone;
    6,6-(1,2-Ethanediyl)-17β-hydroxy-19-nor-17α-pregna-4,20(Z)-dien-3-one-21-carboxylic acid γ-lactone;
    16,16-(1,2-Ethanediyl)-17β-hydroxy-19-nor-17α-pregna-4,20(Z)-dien-3-one-21-carboxylic acid γ-lactone;
    17β-Hydroxy-7α-vinyl-18-methyl-19-nor-17α-pregna-4,20(Z)-dien-3-one-21-carboxylic acid γ-lactone;
    6,6-(1,2-Ethanediyl)-17β-hydroxy-18-methyl-19-nor-17α-pregna-4,20(Z)-dien-3-one-21-carboxylic acid γ-lactone;
    4-Chloro-17β-hydroxy-18-methyl-19-nor-17α-pregna-4,20(Z)-dien-3-one-21-carboxylic acid γ-lactone and
    4-Chloro-17β-hydroxy-19-nor-17α-pregna-4,20(Z)-dien-3-one-21-carboxylic acid γ-lactone.

2. A method for oral contraception comprising administering to subject in need thereof an effective amount of the 17-hydroxy-19-nor-21-carboxylic acid-steroid γ-lactone compound as claimed in claim 1.

3. A medicinal product containing at least one 17-hydroxy-19-nor-21-carboxylic acid-steroid γ-lactone compound as claimed in claim 1 and at least one suitable pharmaceutically harmless carrier substance.

4. The medicinal product as claimed in claim 3, additionally containing at least one estrogen.

5. The medicinal product as claimed in claim 4, characterized in ha the estrogen is ethinylestradiol.

6. The medicinal product as claimed in claim 4, characterized in that the estrogen is estradiol valerate.

7. The medicinal product as claimed in claim 4, characterized in that the estrogen is a natural estrogen.

8. The medicinal product as claimed in claim 7, characterized in that the natural estrogen is estradiol.

9. The medicinal product as claimed in claim 7, characterized in that the natural estrogen is a conjugated estrogen.

10. A medicinal product for intrauterine use, comprising the 17-hydroxy-19-nor-21-carboxylic acid-steroid γ-lactone compound as claimed in claim 1 and at least one additive.

11. An intrauterine system (IUS), comprising the 17-hydroxy-19-nor-21-carboxylic acid-steroid γ-lactone compound as claimed in claim 1 and at least one additive.

* * * * *